US006929797B2

(12) United States Patent
Mazess et al.

(10) Patent No.: US 6,929,797 B2
(45) Date of Patent: Aug. 16, 2005

(54) TARGETED THERAPEUTIC DELIVERY OF VITAMIN D COMPOUNDS

(75) Inventors: Richard B. Mazess, Madison, WI (US); Charles W. Bishop, Madison, WI (US)

(73) Assignee: Bone Care International, Inc., Madison, WI (US)

( * ) Notice: Subject to any disclaimer, the term of this patent is extended or adjusted under 35 U.S.C. 154(b) by 0 days.

(21) Appl. No.: 09/402,636

(22) PCT Filed: Feb. 13, 1998

(86) PCT No.: PCT/US98/02899

§ 371 (c)(1),
(2), (4) Date: Apr. 26, 2000

(87) PCT Pub. No.: WO98/35704

PCT Pub. Date: Aug. 20, 1998

(65) Prior Publication Data

US 2002/0136731 A1 Sep. 26, 2002

Related U.S. Application Data

(60) Provisional application No. 60/038,364, filed on Feb. 13, 1997.

(51) Int. Cl.⁷ .................... A61K 31/592; A61K 31/593; A61K 39/385; C07K 4/12; C07K 1/02
(52) U.S. Cl. .................. 424/195.11; 424/457; 514/167; 530/307; 530/351
(58) Field of Search ............................ 424/195.11, 457; 514/167; 530/307, 351

(56) References Cited

U.S. PATENT DOCUMENTS

| | | | |
|---|---|---|---|
| 2,383,446 | A | 6/1945 | Calcott et al. |
| 3,697,559 | A | 10/1972 | DeLuca et al. |
| 3,741,996 | A | 6/1973 | DeLuca et al. |
| 3,907,843 | A | 9/1975 | DeLuca et al. |
| 4,160,803 | A | 7/1979 | Potts |
| 4,195,027 | A | 3/1980 | DeLuca et al. |
| 4,202,829 | A | 5/1980 | DeLuca et al. |
| 4,225,596 | A | 9/1980 | DeLuca |
| 4,234,495 | A | 11/1980 | DeLuca et al. |
| 4,260,549 | A | 4/1981 | DeLuca et al. |
| 4,292,250 | A | * 9/1981 | DeLuca et al. |
| 4,362,710 | A | 12/1982 | Watanabe |
| 4,391,802 | A | 7/1983 | Suda et al. |

(Continued)

FOREIGN PATENT DOCUMENTS

| | | |
|---|---|---|
| BE | 877 356 | 10/1979 |
| EP | 0197514 | 10/1986 |
| EP | 0390097 | 10/1990 |
| EP | 0503630 | 9/1992 |
| EP | 0512-844 A1 | 11/1992 |
| EP | 0201-057 B1 | 12/1992 |
| EP | 0562497 | 9/1993 |
| EP | 0664287 | 7/1995 |
| JP | 62000033 | 10/1986 |
| JP | 2-104593 | 4/1990 |
| JP | 5320127 | 9/1993 |
| JP | 6025039 | 2/1994 |
| WO | WO 84/04527 | 11/1984 |
| WO | WO 87/00834 | 2/1987 |
| WO | WO 90/10620 | 9/1990 |
| WO | WO 92/05130 | 4/1992 |
| WO | WO 92/12165 | 7/1992 |
| WO | WO 92/14493 | * 9/1992 |
| WO | WO 92/21355 | * 12/1992 |
| WO | WO 93/07883 | 4/1993 |
| WO | WO 93/14763 | 8/1993 |
| WO | WO 94/16711 | 8/1994 |
| WO | WO 96/40153 | 12/1996 |
| WO | WO 99/49870 | 10/1999 |

OTHER PUBLICATIONS

Stryer et al, in Biochemistry, Third Edition, W. H. Freeman and Company, New York, pp. 569–570, 1988.*

Orme et al, Bioorg Med Chem Lett 4: 1375–1380, 1994.*

Bauss et al., Effect of 17beta–estraciol–bisphosphonate conugates, potential bone–seeking estrogen pro–drugs, on 17beta–estradiol serum kinetics and bone mass in rats, Sep. 1996, Calcif Tissue Int 59(3): 168–73.*

Kobayashi et al, Jan. 1997, Anal Biochem 244(2):374–83.*

Holick, M., et al., "Identification of 1,25–Dihydroxycholecalciferol, a Form of Vitamin $D_3$ Metabolically Active in the Intestine", *Proc. Natl. Acad. Sci. USA*, 68:803–804 (1971).

Holick, M., et al., "1α–Hydroxy Derivative of Vitamin $D_3$: A Highly Potent Analog of 1α,25–Dihydroxyvitamin $D_3$", *Science* 180:190–191 (1973).

Jensen, G., et al., "Treatment of Post Menopausal Osteoporosis, A Controlled Therapeutic Trial Comparing Oestrogen/Gestagen, 1,25–Dihydroxy–Vitamin $D_3$ and Calcium" *Clin. Endocrinol.* 16:515–524 (1982).

(Continued)

*Primary Examiner*—Christina Chan
*Assistant Examiner*—Phuong Huynh
(74) *Attorney, Agent, or Firm*—Michael Best & Friedrich LLP; Teresa J. Welch; Gregory J. Hartwig

(57) ABSTRACT

The present invention is directed to a conjugate which includes at least one vitamin D moiety thereof and at least one targeting molecule moiety to pharmaceutical compositions of the conjugate, and to methods for using the conjugate for target-specific delivery of vitamin D or analogs thereof to tissues in need thereof. When a particularly preferred form is administered to a patient, the targeting molecule component of the conjugate of this invention seeks out and binds to a tissue of interest, such as bone or tumor tissue, where the vitamin D has a therapeutic effect.

6 Claims, 9 Drawing Sheets

U.S. PATENT DOCUMENTS

| | | | |
|---|---|---|---|
| 4,508,651 A | | 4/1985 | Baggiolini et al. |
| 4,554,106 A | | 11/1985 | DeLuca et al. |
| 4,555,364 A | | 11/1985 | DeLuca et al. |
| 4,588,716 A | | 5/1986 | DeLuca et al. |
| 4,661,294 A | * | 4/1987 | Holick et al. |
| 4,689,180 A | | 8/1987 | DeLuca et al. |
| 4,698,328 A | | 10/1987 | Neer et al. |
| 4,717,721 A | | 1/1988 | DeLuca et al. |
| 4,833,125 A | | 5/1989 | Neer et al. |
| 4,866,048 A | | 9/1989 | Calverley et al. |
| 4,902,481 A | | 2/1990 | Clark et al. |
| 5,063,221 A | | 11/1991 | Nishii et al. |
| 5,104,864 A | | 4/1992 | DeLuca et al. |
| 5,141,719 A | | 8/1992 | Fernwood et al. |
| 5,157,135 A | | 10/1992 | Tsuji et al. |
| 5,183,815 A | | 2/1993 | Saari et al. |
| 5,205,989 A | | 4/1993 | Aysta |
| 5,219,528 A | | 6/1993 | Clark |
| 5,232,836 A | * | 8/1993 | Bouillon et al. |
| 5,264,184 A | | 11/1993 | Aysta et al. |
| 5,264,618 A | | 11/1993 | Felgner et al. |
| 5,334,740 A | | 8/1994 | Takahashi et al. |
| 5,338,532 A | | 8/1994 | Tomalia et al. |
| 5,372,996 A | | 12/1994 | Labrie |
| 5,403,831 A | | 4/1995 | DeLuca et al. |
| 5,417,923 A | | 5/1995 | Bojanic et al. |
| 5,488,120 A | | 1/1996 | Knutson et al. |
| 5,527,524 A | | 6/1996 | Tomalia et al. |
| 5,554,386 A | | 9/1996 | Groman et al. |
| 5,576,309 A | * | 11/1996 | Tamura et al. |
| 5,597,575 A | | 1/1997 | Breitbarth |
| 5,602,116 A | * | 2/1997 | Knutson et al. |
| 5,614,513 A | | 3/1997 | Knutson et al. |
| 5,637,742 A | | 6/1997 | Valles et al. |
| 5,661,025 A | | 8/1997 | Szoka, Jr. et al. |
| 5,691,328 A | * | 11/1997 | Peterson et al. |
| 5,739,271 A | | 4/1998 | Sridhar et al. |
| 5,795,882 A | | 8/1998 | Bishop et al. |
| 6,309,666 B1 | * | 10/2001 | Hatano et al. |
| 6,521,608 B1 | | 2/2003 | Henner et al. |
| 6,537,982 B1 | | 3/2003 | Bishop et al. |

OTHER PUBLICATIONS

Jones, G. et al., "Isolation and Identification of 1,25–Dihydroxyvitamin $D_2$", *Biochemistry*, 14:1250–1256 (1975).

Köhler, G., et al., "Continuous Cultures of Fused Cells Secreting Antibody Of Predefined Specificity", *Nature* 256:495–497 (1975).

Köhler, G., et al. "Derivation of Specific Antibody–Producing Tissue Culture And Tumor Lines by Cell Fusion", *Eur. J. Immunol.* 6:511–519. (1976).

Lam, H., et al., "1α–Hydroxyvitamin $D_2$: A Potent Synthetic Analog of Vitamin $D_2$", *Science* 486:1038–1040 (1974).

Miller, G., et al., The Human Prostatic Carcinoma Cell Line LNCaP Expresses Biologically Active, Specific Receptors for 1α,25–Dihydroxyvitamin $D_3$, *Cancer Res.* 52:515–520 (1992).

Orimo, H., et al., "Reduced Occurrence of Vertebral Crush Fractures in Senile Osteoporosis Treated with 1α(OH)–vitamin $D_3$", *Bone and Mineral* 3:47–52 (1987).

Ott, S., and Chesnut, C., "Calcitriol Treatment in Not Effective in Postmenopausal Osteoporisis", *Ann. Int. Med.* 110:267–274 (1989).

Ponpipom, M., et al., "Saccharide Receptor–Mediated Drug Delivery", *Receptor–Mediated Targeting of Drugs*, (Gregoriadis et al, ed.) NATO ASI series, 53–71 (1983).

Poznansky, M., et al., "Biological Approaches to the Controlled Delivery of Drugs: A Critical Review", *Pharmacol. Rev.* 36:277–336 (1984).

*Molecular Cloning*, 2nd ed., Sambrook et al., eds., Cold Spring Harbor Lab. Press, 18.3 et seq. (1989).

Shiraki, M., et al., "Long–Term Treatment of Postmenopausal Osteoporosis with Active Vitamin $D_3$, 1–Alpha–Hydroxycholecalciferol (1α–$OHD_3$) and 1,24 Dihydroxycholecalciferol (1,24$(OH)_2)D_3$)", *Endocrinol. Japan* 32:305–315 (1985).

Skowronski, R., et al., "Actions of Vitamin $D_3$ Analogs on Human Prostate Cancer Cell Lines: Comparison with 1,25–Dihydroxyvitamin $D_3$", *Endocrinology* 136:20–26 (1995).

Søresen, O., et al., "Treatment of Senile Osteoporosis with 1α–Hydroxyvitamin $D_3$", *Clin. Endocrinol.* 7:169S–175S (1977).

Aloia, J., et al., "Calcitriol in the Treatment of Postmenopausal Osteoporosis", *Amer. J. Med.* 84:401–408 (1988).

Baggiolini, E., et al., "Stereocontrolled Total Synthesis of 1α,25–Dihydroxyergocalciferol", *J. Org. Chem.*, 51:3098–3108 (1986).

Brewster, M., et al., "Improved Delivery through Biological Membranes. 32.[1] Synthesis and Biological Activity of Brain–Targeted Delivery Systems for Various Estradiol Derivatives", *J. Med. Chem.* 31: 244–249 (1988).

Christiansen, C., et al., "Effect of 1,25–dihydroxy–vitamin $D_3$ in Itself or Combined With Hormone Treatment In Preventing Postmenopausal Osteoporosis", *Eur. J. Clin. Invest.* 11: 305–309 (1981).

Counsell, R., et al., "Lipoproteins as Potential Site–Specific Delivery Systems for Diagnostic and Therapeutic Agents", *J. Med. Chem.* 25:1115–1120 (1982).

Davis, S., et al. "Colloidal Delivery Systems–Opportunities and Challenges", *Site–Specific Drug Delivery*, (Tomlinson et al. eds.), John Wiley, New York, 93–111 (1986).

Gallagher, J. et al., "Treatment of Postmenopausal Osteoporosis with High Doses of Synthetic Calcitriol", *Ann. Int. Med.* 113:649–655 (1990).

Barton, D. et al., "Synthetic Uses of Steroidal Ring & Diene Protection: 22,23–Dihydroergosterol," *JCD Perkin I*, (1976) pp. 821–826.

Beer, T. et al., "Weekly High–Dose Calcitriol and Docetaxel in Metastatic Androgen–Independent Prostate Cancer," *Journal of Clinical Oncology*, (Jan. 2003) 21:1:123–128.

Blazsek, I. et al. "Combined Differentiation Therapy in Myelodysplastic Syndrome with Retinoid Acid, 1α25 Dihydroxyvitamin $D_3$, and Prednisone," 16:4:259–264 (Abstract).

Brautbar, N. "Osteoporosis: Is 1,25–$(OH)2D3$ of Value in Treatment" *Nephron* (1986) 44:161–166.

Braunwald, E. et al., *Harrison's Principles of Internal Medicine:* Part Eleven, "Disorders of Bone and Mineral Metabolism," Chapter 335, McGraw–Hill, New York, (1987) pp. 1860–1865.

Brown, J.P. et al., "Serum Bone Gala–Protein: A Specific Marker for Bone Formation in Postmenopausal Osteoporosis," *Lancet*, (1984) 1:1091–1093.

Caniggia, A. et al., "Effect of a Long–Term Treatment with 1,25–Dihydroxyvitamin $D_3$ on Osteocalcin in Postmenopausal Osteoporosis," *Cacified Tissue Int.*, (1986) 38:328–332.

Christiansen, C. et al., "Prevention of Early Postmenopausal Bone Loss: Controlled 2–Year Study in 315 Normal Females," *Europ J Clin Inves.*, (1980) 10:273–279.

Crump, D.R. et al., "(22S)–Hydroxyvitamin $D_4$," *J.C.S. Perkins Trans. I*, (1973) pp. 2731–2733.

Cho, Y.L. et al., "Combined Effects of 1,25–Dihydroxyvitamin $D_3$ and Platinum Drugs on the Growth of MCF–7 Cells," *Cancer Research*, (Jun. 1991) 51:2848–2853.

Defacque, H. et al., "Different Combinations of Retinoids and Vitamin $D_3$ Analogs Efficiently Promote Growth Inhibition and Differentiation of Myelomoncytic Leukemia Cell Lines," *J. Pharmacology and Experimental Therapeutics*, (1994) 271:193–199.

DeLucca et al., "Synthesis, Biological Activity, and Metabolism of 22,23–$^3$H–Vitamin $D_4$," *Arch. Biochem, Biophys.*, (1968) 124:122–128.

Duda et al., "1,25–Dihydroxyvitamin D Stimulation Test for Osteoblast Function in Normal and Osteoporotic Postmenopausal Women," *J. Clinic. Inves.*, (1987) 79: 1249–1253.

Endo, K. et al., "Effect of Combination Treatment with Vitamin D Analog (OCT) and a Bisphosphonate (AHPrBP) in a Nude Mouse Model of Cancer–Associated Hypercalcemia," *Journal of Bone and Mineral Research*, (1998) 13:9:1378–1383.

Folders, J. et al., "Long Term Treatment with $1\alpha$ (OH)$D_3$ for Postmenopausal Osteoporosis: Efficacy and Saftey," *Osteoporosis*, (1987) 2:971–973.

Gallagher, J.C. et al., "Effects of Increasing Doses of $1\alpha$–Hydroxyvitamin $D_2$ on Calcium Homeostasis in Postmenopausal Osteopenic Women," *J. Bone Min. Res.*, (1994) 9:5:607–614.

Grab, W. Z. *Physiol. Chem.*, (1936) 243:63–89.

Guidelines for the Clinical Evaluation of Drugs Used in the Treatment of Osteoporosis, HEW (FDA) 80–3094, (1979) pp. 5–6.

Hershberger, P. et al. "Calcitriol (1,25–Dihydroxycholecalciferol) Enhances Paclitaxel Antiumor Activity in Vitro and in Vivo and Accelerates Paclitaxel–induced Apoptosis," *Clinical Cancer Research*, (Apr. 2001) 7:1043–1051.

Hoikka, V. et al., "Treatment of Osteoporosis with 1–Alpha–Hydroxycholecalciferol and Calcium,"*Acta. Med. Scand.*(1980) 207:221–224.

Holick, M.F., "Noncalcemic Actions of 1,25–Dihydroxyvitamin $D_3$ and Clinical Applications", *Bone*, (1995) 17:2:107S–110S.

Horst et al., "Quantitation of Vitamin D and its Metabolites and Their Plasma Concentrations in Five Species of Animals," *Anal. Biochem.*, (1981) 116:189–203.

Horst et al., "Discrimination in the Metabolism of Orally Dosed Ergocalciferol and Cholecalciferol by the Pig, Rat and Chick," *Biochem. J.*, (1982) 204:185–189.

Johnson, C. et al., "Vitamin D–related Therapies in Prostate Cancer," *Cancer and Metastasis Review 21*, (2002) pp. 147–158.

Kanis, J.A. et al., "Guidelines for Clinical Trials in Osteoporosis, A Position Paper of the European Foundation for Osteoporosis," *Osteoporosis Int.*, (1991) 1:182–188.

Kim, S. et al., Potentiation of 1,25–Dihydroxyvitamin $D_3$–Induced Differentiation of Human Promyelocytic Leukemia Cells into Monocytes by Costunolide, a Germacranolide Sesquiterpene Lactone, *Biochem. Pharmacology*, (2002) 64:1233–1242.

Knutson, et al., "Metabolism of 1 $\alpha$–Hydroxyvitamin $D_2$ to activated Dihydroxyvitamin $D_2$ Metabolites Decreases Endogenous $1\alpha$,25–Dihydroxyvitamin $D_3$ in Rats and Monkeys," *Endocrinology*, (1995) 136:11:4749–4753.

Kocienski, P.J. et al., "Calciferol and its Relatives. A Synthesis of Vitamin $D_4$," *J.C.S. Perkins I*, (1979) pp. 1290–1293.

Lam, H.Y. et al., *Science*, (1974) 486:1038–1040.

Majewski, et al., "Inhibition of Tumor Cell–Induced Angiogenisis by Retinoids, 1,25–Dihydroxyvitamin $D_3$ and their Combination," *Cancer Letters*, (1993) 75:35–39.

Martin and DeLuca, "Calcium Transport," *Am. J. Physiol.*, 216:1352–1359.

Mathias, C.J. et al., "Tumor–Selective Radiopharmaceutical Targeting Via Receptor–Mediated Endocytosis of Gallium–67–Deferoxamine–Folate," *J. Nucl. Med.* (1996), 37(6):1003–1008.

McDonald, F.G., "The Multiple Nature of Vitamin D," *J. Biol. Chem.* 114, (1936) 1xv.

*Merck Index*, S. Budavari (ed.), 11th ed., Merck & Co., Rahway, N.J. (1989) pp. 1579, #9930.

Moffatt, K. et al., "$1\alpha$,25–Dihydroxyvitamin $D_3$ and Platinum Drugs Act Synergistically to Inhibit the Growth of Prostate Cancer Cell Lines," *Clinical Cancer Research*, (Mar. 1995) 5:695–703.

Muindi, J. et al., "Pharmacokinetics of High–Dose Oral Calcitriol: Results From a Phase 1 Trial of Calcitriol and Paclitaxel," *Clinical Pharmacology & Therapeutics*, (Dec. 2002) pp. 648–659.

Nemeto, H. et al., "A Stereoselective Synthesis of 1 $\alpha$—Hydroxy–Vitamin $D_3$," *Chemistry Letters*, (1985) 8:1131–1132.

Paaren et al., "Direct C(1) Hydroxylation of Vitamin $D_3$ and Related Compounds," *J. Org. Chem.*, (1980) 45:3253.

Packman, K. et al. "Combination Treatment of MCF–7 Xenografts with the Vitamin $D_3$ Analog EB1089 and Antiestrogens," (Vitamin D Endocrine Workshop, Nashville, TN May 27–Jun. 1, 2000) pp. 511–514.

Podenphant, J. et al., "Scrum Bone Gla Protein and Other Biochemical Estimates of Bone Turnover in Early Postmenopausal Women During Prophylactic Treatment for Osteoporosis," *Acta Med Scand*, (1985) 218:329–333.

*Physican's Desk Reference*, Edition 43:1746–1748.

Pouilles, J.M. et al., "Prevention of Early Postmenopausal Bone Loss with $1\alpha$–Hydroxy Vitamin $D_3$, A Three–Year Prospective Study," *Clin Rheumatol.* 11, 4 (1992) pp. 492–497.

Ravid, A. et al., "1,25–Dihydroxyvitamin $D_3$ Enhances the Susceptibility of Brease Cancer Cells to Doxorubicin–induced Oxidative Damage," *Cancer Research*, (Feb. 15, 1999) 59:862–867.

Reeve, L.E. et al., "Biological Activity of $1\alpha$–hydroxy Vitamin $D_2$ in Rat," *Arch. Biochem. Biophys.* (Feb. 1978) 186:1:164–167.

Sato, F. et al., "Biological Activity of $1\alpha$,25–Dihydroxyvitamin D Derivatives—24–epi–$1\alpha$,25–Dihydroxyvitamin D–2 and $1\alpha$,25–Dihydroxyvitamin D–7," *Biochem. Biophys. Acta*, (1991) 1091:188–192.

Shiraki, M. et al., *Endocrinol. Japan*, (1985) 32:305–315.

Siwinska, A. et al. "Potentiation of the Antiproliferative Effect in Vitro of Doxorubicin, Cisplatin and Genistein by New Analogues of Vitamin D,"*Anticancer Research*, (2001) 21:1925–1929.

Sjoden et al., "Effects of 1 OHD$_2$ on Bone Tissue," *Acta. Endocrinol.* (Copenh.) (Aug. 1984) 16:4:564–568.

Sjoden, G. et al., "Antirachitic Activity of 1α-Hydroyergocalciferol and 1α-Hydroxycholecalciferol in Rats," *J. Nutr.*, (1984) 114:2043–2046.

Sjoden, G. et al., "1α-Hydroxyvitamin D$_2$ is Less Toxic than 1α-Hydroxyvitamin D$_3$ in the Rat," *Proc. Soc. Exp. Biol. Med.*, (1985) 178:432–436.

Skowronski et al., "Vitamin D and Prostate Cancer: 1,25 Dihydroxyvitaim D$_3$ Receptors and Actions in Human Prostate Cancer Cell Lines," *Endocrinology*, (1993) 132:1952–1960.

Slapak, C. et al., "Treatment of Acute Myeloid Leukemia in the Elderly with Low–Dose Cytarabine, Hydroxyurea, and Calcitriol," *Amer. J. Hematology*, (1992) 41:178–183.

Sommerfeldt et al., "Metabolism of Orally Administered [$^3$H]Ergocalciferol and [$^3$H]Cholecalciferol by Dairy Calves,"*J. Nutr.*, (1983) 11:2595–2600.

Song, X.D. et al., "Bryostatin–1 and 1–α,25–Dihydroxyvitamin D$_3$ Synergistically Stimulate the Differentiation of NB4 Acute Promyelocytic Leukemia Cells," *Leukemia*, (1999) 13:275–281.

Studzinski, G. et al., "Potentiation by 1–α,25–Dihydroxyvitamin D$_3$ of Cytotoxicity to HL–60 Cells Produced by Cytarabine and Hydroxyurea," *J. National Cancer Inst.*, (Apr. 1986) 76:4:641–648.

Strugnell et al., "Metabolism of a Cyclopropane–Ring–Containing Analog to 1α-Hydroxyvitamin D$_3$ in a Hepatocyte Cell Model," *Biochem. Pharm.*, (1990) 40:333–341.

Strugnell et al., "1 α,24(S)–Dihydroxyvitamin D$_2$: a biologically active product of 1 α–hydroxyvitamin D$_2$ made in the human hepatoma, Hep3B," *Biochem. J.*, (1995) 310:233–241.

Suzuki, Y. et al., "The Enhancement of the Chemotherapeutic Effects on Human Prostate Cancer Cell–The Combination with the Growth Factor Interaction Inhibitor (Suramin)," *Acta Urologica* (1993) 12:1215–1220, (Abstract).

Swami, S. et al., "1α,25–Dihydroxyvitamin D$_3$ Down–Regualtes Estrogen Receptor Abundance and Suppresses Estrogen Actions in MCF–7 Human Breast Cancer Cells," *Clinical Cancer Research*, (Aug. 2000) 6:3371–3379.

Tachibana, Y. (Nisshin Flour Milling Co.), "Preparation of 1Beta–Hydroxyvitamin D$_2$ and D$_3$," *Chemical Abstracts*, (1990) 113:1:6688 Col. 2 Abstract No. 6683y.

Tanaka, Y. et al., *Endocrinology* (1973) 92:417–422.

Torres, R. et al., Etoposide Stimulates 1,25–Dihydroxyvitamin D$_3$ Differentiation Activity, Hormone Binding and Hormone Receptor Expression in HL–60 Human Promyelocytic Cells, *Molecular and Cellular Biochemistry*, (2000) 208:157–162.

Tsuji, M. et al., "Synthesis of 22,23–Dihydro–1α,25–Dihydroxyvitamin D$_2$ and its 24R–Epimer, New Vitamin D$_2$ Derivatives," *Bull. Chem. Soc. Jpn.*, (1990) 63:8:2233–2238.

Wang, Q. et al., "1,25–Dihydroxyvitamin D$_3$ and All–trans-s–Retinoic Acid Sensitize Breast Cancer Cells to Chemotherapy–induced Cell Death," *Cancer Research*, (Apr. 2000) 60:2040–2048.

Wang, X. et al., "Inhibition of p38 MAP Kinase Activity Up–Regulates Multiple MAP Kinase Pathways and Potentiates 1,25–Dihydroxyvitamin D$_3$–Induced Differentiation of Human Leukemia HL60 Cells," *Experimantal Cell Research*, (2000) 258:425–437.

Wietroub, S. et al. "The Dichotomy in the Effects of 1,25 Dihydroxy Vitamin D$_3$ and 24, 25 Dihydroxy Vitamin D$_3$ on Boen Gamma–Carboxyglutamic Acid–Containing Protein in Serum and Bone in Vitamin D–Deficient Rats," *Calcuf, Tissue Int.*, (1987) 40:166–172.

Windaus, A. et al., "Uber das Krystallisierte Vitamin D$_4$,"*Z. Physiol. Chem.*, (1937) 247:185–188.

Yu, W. et al., "Enhancement of 1,25—Dihydroxyvitamin D$_3$– Mediated Antitumor Activity with Dexamethasone," *J. National Cancer Inst.*, (Jan. 1998) 90:2:134:141.

Zerwekh et al., "Short–Term 1,25–Dihydroxyvitamin D$_3$ Administration Raises Serum Osteocalcin in Patients with Postmenopausal Osteoporosis," *J. Clin. Endocrinol. Metabol*, (1985) 60:615–617.

Londowski J.M., Kost S.B. et al., "Biological activity of the C–1, C–3, C–25, beta–D glucopyranosides of 1,25–dihydroxyvitamin D3", J. Pharmol. Exp. Ther., vol. 237, No. 3, 1986, pp. 837–840.

Beer, et al., "A Phase 1 Trial of Pulse Calcitriol in Patients with Refractory Malignancies," *Cancer*, vol. 91, No. 12 (Jun. 15, 2001) 2431–2439.

Beer, et al., "Weekly High–Dose Calcitriol and Docetaxel in Advanced Prostate Cancer," *Seminars in Oncology*, vol. 28, No. 4., Suppl 15 (Aug. 2001) 49–55.

* cited by examiner 1,25-(OH)$_2$D$_3$

TARGETED THERAPEUTIC DELIVERY OF VITAMIN D COMPOUNDS

CROSS-REFERENCE TO RELATED APPLICATIONS

This application claims the benefit of the priority date, under 35 U.S.C. § 119, of U.S. Provisional Application No. 60/038,364, filed 13 Feb. 1997.

STATEMENT REGARDING FEDERALLY SPONSORED RESEARCH OR DEVELOPMENT

Not applicable

BACKGROUND OF THE INVENTION

This invention relates generally to the targeted therapeutic delivery of vitamin D compounds and, in particular, delivery to bone and tumor tissue.

Too often the practicing clinician is faced with an unresolvable dilemma. To effectively achieve therapy against a disease, it becomes necessary to balance the devastation wrought by the illness against the noxious effects conferred by the drugs used to treat it. Although therapy should represent a complete tolerance to the dose regimen, in absolute terms it frequently delineates a compromise position, thereby effecting only an "acceptable" level of treatment.

In the absence of preventive measures to combat the onset of disease, the next ideal alternative is to design a drug that specifically recognizes the origin of the disorder and then corrects it. This so-called "magic bullet" or site-specific drug delivery concept is not a new concept. Such a concept is directed to linking the action of drugs to specific receptor-mediated events. These concepts still serve as a primary foundation for the continuing development of drugs and antibodies.

Chemical modification of a drug, in some cases enhances its target organ specificity. For example, brain-targeted delivery systems based on the dihydropyridine-pyridinium salt redox interconversion have been developed for compounds such as estradiol and ethinylestradiol. Brewster et al., 31 *J. Med. Chem.* (1988) 244. Covalent coupling of some sugars to drugs can enhance their uptake by the liver. Ponpinom et al., in *Receptor Mediated Targeting of Drugs*, (Gregoriadis et al, eds.) NATO ASI series, Plenum Press, New York, 1983, p. 53.

In most cases, however, a specific carrier is needed that is designed for transport and delivery of the drug to its target tissue. In such cases, the distribution characteristics of the drug itself are irrelevant, since the carrier characteristics determine whether the drug is delivered to the target cells. However, once delivered to the target cells, it still will be necessary to consider the distribution of the drug at its intracellular effect site.

A number of particles have been proposed as drug carrier systems. Recent interest has focused on monoclonal antibodies and colloidal delivery systems such as liposomes and polymeric microspheres. See, e.g., Davis et al. in *Site-Specific Drug Delivery*, (Tomlinson et al. eds.), John Wiley, New York, 1986, p. 93.

Soluble molecules have also been proposed as drug carriers, including DNA, lectins, poly-L-lysine, virosomes, insulin, dextran, HCG, dipeptides and even cellular systems such as erythrocytes and fibroblasts. See, e.g., Poznansky et al., 36 *Pharmacol. Rev.* (1984) 277. Still others have suggested and attempted to use lipoproteins as drug carriers, especially low-density lipoproteins. See, e.g., Counsell et al., 25 *J. Med. Chem.* (1982) 1115.

Obviously, the need for site-specific drug delivery is highest in pathological conditions such as cancer and severe viral infections. Side effects of the drugs utilized in the treatment of neoplastic diseases often are quite severe. Other fast-growing tissues such a bone marrow and gastrointestinal border cells are affected by the antineoplastic drug, and therapy will often have to be stopped.

The need for site-specific drug delivery is also high in bone conditions, particularly osteoporosis. With the recognition that osteoporosis occurs to some extent in all postmenopausal women, the site-specific delivery of bone agents to the mineralized bone matrix has been proposed. Certain agents are known for their bone-seeking characteristics or bone affinity, and the linkage of such bone-seeking agents to enzymes, steroids, or hormones to provide a bone-specific drug delivery agent has been advanced. For example, it has been proposed to join a bone-seeking agent, such as tetracycline, to a carbonic anhydrase inhibitor through a bridging agent to provide compounds for the treatment of or prophylaxis of degenerative bone diseases. See, European Patent Application No. 201,057.

Further, it has been taught to link a hormone, e.g., calcitonin or insulin-like growth factor, to an amino methylene bisphosphonic acid. See, Japanese Patent Application No. 2104-593A. U.S. Pat. No. 5,183,815 discloses that the linkage of a steroid to an alkyl bisphosphonic acid can exhibit a localized therapeutic effect on bone. European Patent Application No. 0 512 844 A1 discloses linkage of a bone growth factor, such as transforming growth factor-beta, to bone-targeting molecules such as tetracycline, calcitonin, bisphosphonates, polyaspartic acid, polyglutamic acid, aminophosphosugars, or estrogens to provide a local bone-augmenting formation agent.

Vitamin D has long been established as having an important biologic role in bone and mineral metabolism. It is well known that vitamin D plays a critical role in stimulating calcium absorption and regulating calcium metabolism. The discovery of active forms of vitamin D, (M. F. Holick et al., 68 *Proc. Natl. Acad. Sci. USA*, 803–804 (1971); G. Jones et al., 14 *Biochemistry*, 1250–1256 (1975) and active vitamin D analogs (M. F. Holick et al., *Science* 180, 190–191 (1973); H. Y. Lam et al., *Science* 186, 1038–1040 (1 974)), caused much excitement and speculation about the usefulness of these vitamin D compounds in the treatment of bone depletive disorders.

Animal studies examining the effects of these active vitamin D compounds suggested that such agents would be useful in restoring calcium balance. Further, an early clinical study indicated that administration of 0.5 $\mu$g/day of 1$\alpha$,25-dihydroxyvitamin $D_3$, the hormonally active form of vitamin $D_3$, to a group of postmenopausal women improved the intestinal calcium absorption as well as the calcium balance in the women. On this basis, U.S. Pat. No. 4,225,596 ("596 Patent") described and claimed the use of 1$\alpha$,25-dihydroxyvitamin $D_3$ for increasing calcium absorption and retention. Such use also was claimed in the same patent for 1,25-dihydroxyvitamin $D_2$, and 1$\alpha$-hydroxyvitamin $D_2$, which compounds, the patent teaches, are "eminently suitable and readily substitutable for the 1,25 dihydroxycholecalciferol [1$\alpha$,25-dihydroxyvitamin $D_3$]."

The best indicator of the efficacy of vitamin D compounds in the prevention or treatment of depletive bone disorders, however, is bone itself rather than calcium absorption or calcium balance. More recent clinical data indicates that, at the dosage ranges taught in the '596 Patent, 1α,25-dihydroxy-vitamin $D_3$ has, at best, modest efficacy in preventing or restoring loss of bone mass or bone mineral content (S. M. Ott and C. H. Chesnut, *Ann. Int. Med.* 110:267–274 (1989); J. C. Gallagher et al., *Ann. Int. Med.* 113:649–655 (1990); J. Aloia et al., *Amer. J. Med.* 84:401–408 (1988)).

These clinical studies with 1α,25-dihydroxyvitamin $D_3$, and another conducted with 1α-hydroxyvitamin $D_3$ (M. Shiraki et al., *Endocrinol. Japan* 32, 305–315 (1 985)), indicate that the capacity of these two vitamin D compounds to restore lost bone mass or bone mineral content is dose-related. These studies also indicate, however, that at the dosage ranges required for either of the compounds to be truly effective, toxicity in the form of hypercalcemia and hypercalciuria becomes a major problem. Specifically, attempts to increase the amount of 1α,25-dihydroxyvitamin $D_3$ above 0.5 μg/day have frequently resulted in toxicity. At dosage levels below 0.5 μg/day, no effects are observed on bone mass or mineral content. (See G. F. Jensen et al., *Clin. Endocrinol.* 16, 515–524 (1 982); C. Christiansen et al., *Eur. J. Clin. Invest.* 11, 305–309 (1981)). Two μg/day of 1α-hydroxyvitamin $D_3$ was found to have efficacy in increasing bone mass in patients exhibiting senile osteoporosis (O. H. Sorensen et al., *Clin. Endocrinol.* 7, 169S–175S (1977)). Data from clinical studies in Japan, a population that has low calcium intake, indicate that efficacy is found with 1α-hydroxyvitamin $D_3$ when administered at 1 μg/day (M. Shiraki et al., *Endocrinol. Japan.* 32:305–315 (1985); H. Orimo et al., *Bone and Mineral* 3, 47–52 (1987)). At 2 μg/day, however, toxicity with 1α-hydroxy-vitamin $D_3$ occurs in approximately 67 percent of the patients, and at 1 μg/day, this percentage is approximately 20 percent.

More recently, other roles for vitamin D have come to light. Specific nuclear receptors for 1α, 25-dihydroxyvitamin $D_3$ have been found in cells from diverse organs not involved in calcium homeostasis. For example, Miller et al., 52 *Cancer Res.* (1992) 515–520, have demonstrated biologically active, specific receptors for 1α,25-dihydroxyvitamin $D_3$ in the human prostatic carcinoma cell line, LNCaP.

More specifically, it has been reported that certain vitamin D compounds and analogs are potent inhibitors of malignant cell proliferation and inducers/stimulators of cell differentiation. For example, U.S. Pat. No. 4,391,802 issued to Suda et al. discloses that 1α-hydroxyvitamin D compounds, specifically 1α,25-dihydroxyvitamin $D_3$ and 1α-hydroxyvitamin $D_3$, possess potent antileukemic activity by virtue of inducing the differentiation of malignant cells (specifically leukemia cells) to nonmalignant macrophages (monocytes), and are useful in the treatment of leukemia. In another example, Skowronski et al., 136 *Endocrinology* (1 995) 20–26, have reported antiproliferative and differentiating actions of 1α,25-dihydroxyvitamin $D_3$ and other vitamin $D_3$ analogs on prostate cancer cell lines.

Previous proliferation studies, such as those cited above, focused exclusively on vitamin $D_3$ compounds. Even though such compounds may indeed be highly effective in differentiating malignant cells in culture, their practical use in differentiation therapy as anticancer agents is severely limited because of their equally high potency as agents affecting calcium metabolism. At the levels required in vivo for effective use as antileukemic agents, these same compounds can induce markedly elevated and potentially dangerous blood calcium levels, by virtue of their inherent calcemic activity. That is, the clinical use of 1α,25-dihydroxyvitamin $D_3$ and other vitamin $D_3$ analogs as anticancer agents is precluded, or severely limited, by the risk of hypercalcemia. This indicates a need for compounds with greater specific activity and selectivity of action, i.e., vitamin D compounds with antiproliferative and differentiating effects but which have less calcemic activity than therapeutic amounts of the known compounds or analogs of vitamin D.

Virtually nothing in the art proposes materials or methods for the targeted delivery of vitamin D compounds to specific target tissue, e.g., bone or malignancy sites, such as prostatic cancer cells.

BRIEF SUMMARY OF THE INVENTION

The present invention provides conjugates of vitamin D compounds or analogs and a targeting molecule, having an ability for site-specific delivery of the vitamin D. Specific conjugates include a bone-therapeutic conjugate and an anti-tumor conjugate. The present invention also provides pharmaceutical formulations of such a conjugate, and methods of site-specific delivery of a vitamin D moiety of the conjugate to a tissue of interest in a patient. The present invention provides surprisingly useful means for delivery of vitamin D compounds, analogs or derivatives to tissues of interest (i.e., to target tissue).

The conjugates of the present invention comprises at least one vitamin D moiety associated with a target molecule moiety having an affinity for the target tissue. In one embodiment of the invention, the conjugate includes at least one vitamin D moiety associated with the target molecule moiety via at least one connecting group, such as a bond between the vitamin D moiety and the target molecule moiety, a bifunctional connector, or other connectors such as a biotin-avidin linkage. In another embodiment, the conjugate includes a target molecule moiety having an affinity for the tissue of interest, associated with at least one vitamin D moiety and with a second therapeutic agent other than vitamin D.

The pharmaceutical compositions of the present invention include a conjugate of at least one vitamin D moiety associated with at least one target molecule moiety, and a suitable pharmaceutically acceptable carrier.

In another embodiment, the present invention provides a method for site-specific delivery of vitamin D or an analog of vitamin D, a method which includes administering to a patient a therapeutically effective dose of a conjugate in a pharmaceutically acceptable carrier, wherein the conjugate has at least one vitamin D moiety associated with at least one target molecule via a connector, and wherein the target molecule has an affinity for a tissue of interest. The method is designed to effect site-specific delivery of the vitamin D moiety to the tissue of interest in the patient.

The conjugate, pharmaceutical composition and method of this invention allow for target-specific delivery of vitamin D to a specific tissue in a patient. By specifically targeting and delivering a vitamin D compound as part of the conjugates of this invention, one can effect delivery of the compound to the targeted tissue by administering relatively small amounts of the conjugate to a patient compared to delivery of the same amount of the compound by administration of the compound itself. By reducing the amount of vitamin D compound administered, the present invention significantly reduces the risk of hypercalcemia and other side-effects of administration of vitamin D compounds or analogs to patients using conventional means of administration.

Other advantages and a fuller appreciation of specific adaptations, compositional variations, and physical attributes will be gained upon an examination of the following detailed description of preferred embodiments, taken in conjunction with the figures of the drawing. It is expressly understood that the drawings herein are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawings, wherein like designations refer to like elements throughout, and in which.

DETAILED DESCRIPTION OF THE INVENTION

Figure 1:
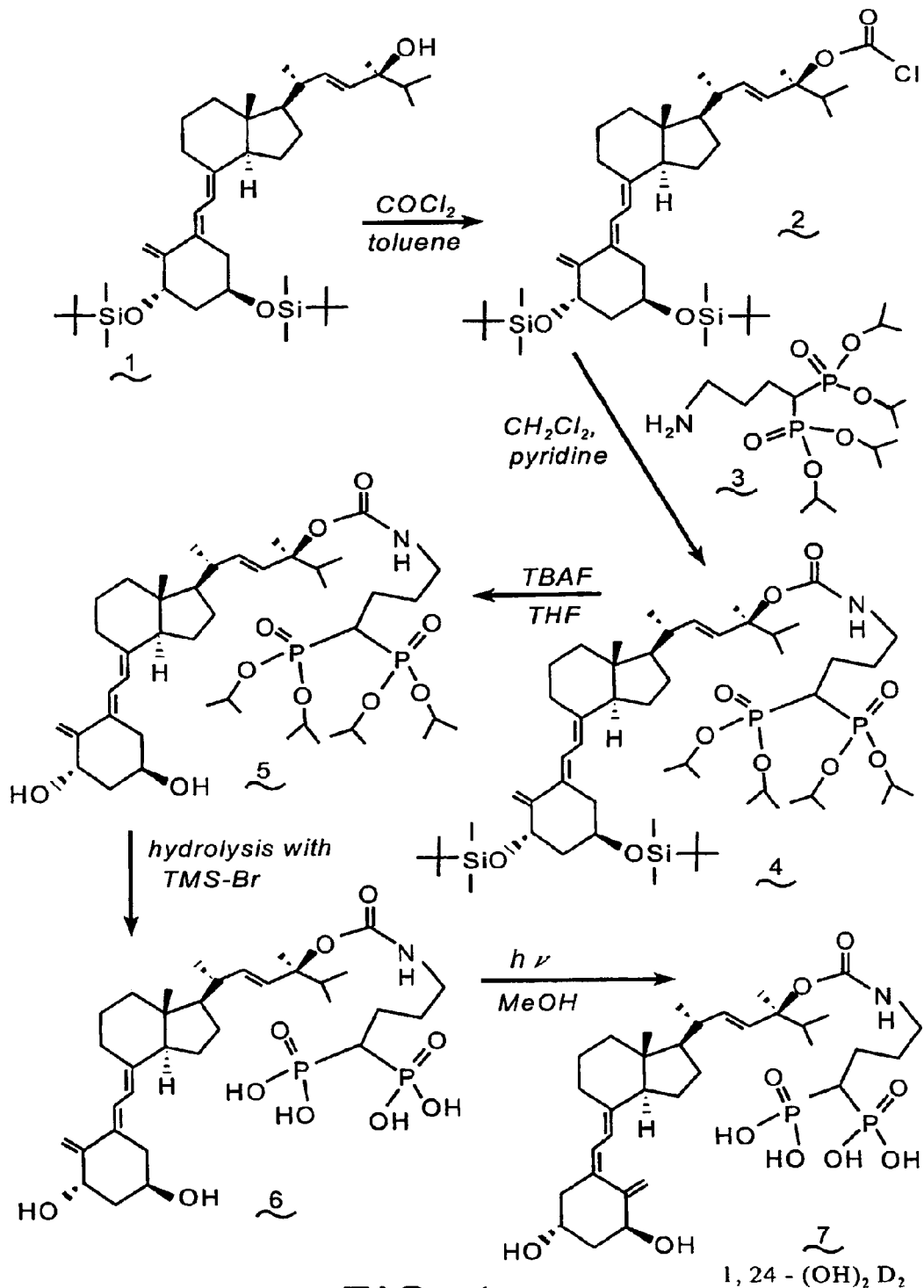
FIG. 1 illustrates a reaction scheme for the preparation of a conjugate of 1α,24-dihydroxyvitamin $D_2$ ("1α,24-$(OH)_2$ $D_2$") and aminoalkyl-1,1-bisphosphonate linked at C-24 of the vitamin D moiety.

The present invention relates to the use of vitamin D formulations in targeting applications. However, the present invention is most particularly adapted for use in site-specific delivery of vitamin D to bone and tumor cells. Accordingly, the present invention will now be described in detail with respect to such endeavors. However, those skilled in the art will appreciate that such a description of the invention is meant to be exemplary only and should not be viewed as limiting the full scope thereof.

The present invention is characterized by an ability for site-specific targeting of vitamin D compounds using conjugates of vitamin D and a targeting molecule having affinity for a tissue of interest. For example, a conjugate of vitamin D and a bone affinity agent is designed to transport and deliver vitamin D to bone. These attributes are achieved through a novel combination of physical and chemical features.

In the following description of the invention, process steps are carried out at room temperature and atmospheric pressure, unless otherwise specified.

As used herein, the term "target molecule" or "targeting molecule" refers to a molecule that binds to or influences metabolism of the tissue of interest. For example, bone-targeting agents may include bone-seeking molecules such as tetracycline, calcitonin, bisphosphonates, chelators, phosphates, polyaspartic acid, poiyglutamic acid, aminophosphosugars, peptides known to be associated with mineral phase of bone such as osteonectin, bone sialoprotein and osteopontin, protein with bone mineral binding domains, and the like. Bone-targeting molecules may also include molecules which themselves affect bone resorption and bone formation rates, such as bisphosphonates, estrogens and other steroids, such as dehydroepiandrosterone (DHEA). These bone-seeking molecules may also possess bone growth therapeutic properties and/or result in a synergistic or additive effect with the vitamin D compound on bone resorption or formation. Skin-seeking molecules include certain metal ion-amino acid chelates; prostate-seeking molecules include certain steroids such as DHEA. Tumor-seeking agents include certain antibodies.

As used herein, the terms "tissue of interest" or "target tissue" are meant to refer to a desired target or site in the body for treatment or for placement of a vitamin D compound or analog. The term "treat" or "treatment" is meant to refer to repair, prevention, alleviation, amelioration, prophylaxsis of a diseased or defective tissue of interest as well as inhibition of abnormal growth, such as hyperproliferafion of cells, and promotion of cell differentiation.

As used herein, the term "therapeutic agent" refers to a material which has or exhibits healing powers when administered to or delivered to the tissue of interest. The term "bone-therapeutic agent" is used herein to refer to a specific type of therapeutic agent, one which ameliorates bone diseases or disorders when delivered or administered to bone. Examples of bone-therapeutic agents include vitamin D compounds, conjugated estrogens or their equivalents, antiestrogens, calcitonin, bisphosphonates, calcium supplements, cobalamin, pertussis toxin, boron and other bone growth factors such as transforming growth factor beta, activin or bone morphogenic protein.

The conjugates in accordance with the present invention include at least one vitamin D compound, analog, component, or moiety (herein designated as "D") associated with at least one target molecule moiety (herein designated as "T") and include those represented by formula (I):

$$(D)_m*(T)_n \qquad (I)$$

wherein n and m represent integers of 1 or greater; and * indicates that the target molecule moiety (T) is associated with the vitamin D compound, analog, component or moiety (D). It is understood that as used herein, the term "vitamin D" includes all compounds having the conventional vitamin D structure of A, C and D rings and C-17 side chain as well as previtamin D compounds which are the thermal isomers of their corresponding vitamin D forms, in which the basic structures may be substituted, unsubstituted or modified, e.g., 19-nor compounds. It is also understood that the vitamin D moiety maintains its biological effectiveness in the conjugate, e.g., its beneficial effect with respect to bone, or in the case of the previtamin D, isomerizes to its corresponding D form having the biological effectiveness.

As used herein, the terms "associated with" or "association" are meant to refer to attachment or linkage of one component of the conjugate (e.g., the vitamin D moiety) or vitamin D moiety and connector to another component of the conjugate, e.g., the target molecule or target molecule and connector, via covalent bonding, hydrogen bonding, metallic bonding, van-der Wall forces, ionic bonding, coulombic forces, hydrophobic or hydrophilic forces, adsorption or absorption, chelate type association, or any combination thereof. The terms "moiety" and "component" used in connection with vitamin D or D, or in connection with target molecule moiety or T, are meant to refer to vitamin D or target molecule in the conjugated forms disclosed herein, i.e., after association occurs. Association between the vitamin D analog and the target molecule may occur at any position on the vitamin D analog molecule depending on the functionality of the target molecule. For example, a bisphosphonate or amide may suitably link at positions on the vitamin D compound or vitamin D analog molecule having a hydroxyl group, such as at C-1, C-3, C-24, C-25.

Vitamin D compounds and analogs operable in the present invention are suitably represented by formula (II):

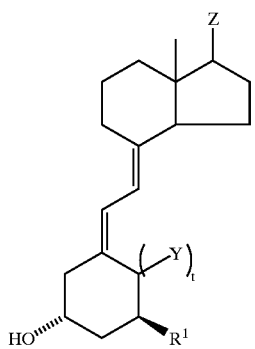

(II)

wherein $R^1$ is H or OH; Z represents a saturated or unsaturated, substituted or unsubstituted, straight-chain or branched $C_1$–$C_{18}$ hydrocarbon group; Y is a =$CH_2$ group; and t is 0 or 1, such that when t is 0, the compound of formula (II) is a 19-nor compound. Preferably, Z is a side chain represented by formula (IIIA):

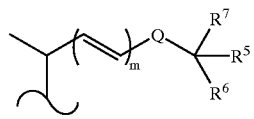

(IIIA)

wherein m is 0 or 1; $R^5$ is H or OH; $R^6$ and $R^7$ are independently H, OH, lower alkyl, lower fluoroalkyl, O-lower alkyl, O-lower acyl, O-aromatic alkyl, lower cycloalkyl or, taken together with the carbon to which they are bonded (i.e., C-25), form a $C_3$–$C_8$ cyclohydrocarbon ring; and Q is —C=C—, —C≡C—, or,

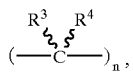

wherein n is 0 or an integer from 1 to 7, $R^3$ is $CH_3$ or H, and $R^4$ is H or OH. For example, Z includes a cholesterol or ergosterol side chain represented by formula (IIIB):

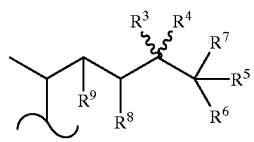

(IIIB)

wherein $R^8$ and $R^9$ are each H or taken together form a double bond between C-22 and C-23, $R^3$ is $CH_3$ or H; $R^4$ and $R^5$ are independently H or OH; and $R^6$ and $R^7$ are independently H, OH, lower alkyl, lower fluoroalkyl, O-lower alkyl, O-lower acyl, O-aromatic acyl, lower cycloalkyl or taken together with the carbon to which they are bonded (i.e., C-25) form a $C_3$–$C_8$ cyclocarbon ring.

Also included as vitamin D compounds within the scope of the present invention are previtamin D compounds, preferably 1α-hydroxyprevitamin D which may include the common cholesterol and ergosterol side chains that may optionally be substituted, preferably hydroxysubstituted, e.g., at C-24 or C-25. Previtamin D compounds are the thermal isomers of the corresponding vitamin D compounds, e.g., 1α-hydroxy previtamin $D_3$ is the thermal isomer of 1α-hydroxy vitamin $D_3$, and exists in thermal equilibrium with same.

Preferred among the target molecules are those which when used as a component of the conjugate of formula (I) result in at least a portion of the conjugate, specifically the vitamin D component of the conjugate, being delivered to a desired target (e.g., a targeted cell, a targeted organ, a tumor, etc.). The preferred target molecules include chemical functionalities exhibiting target specificity, hormones (e.g., biological response modifiers), and antibodies, preferably, monoclonal or polyclonal antibodies, or antibody fragments having the requisite target specificity. Included among the preferred target molecules exhibiting specific affinity for bone are bisphosphonates, tetracycline, polymalonates and dehydroepiandrosterone.

The conjugates of formula (I) are prepared under conditions (such as particular pH, temperature or salt concentrations) which are not detrimental to the particular conjugate components and in the presence of a suitable solvent when required. To control pH, a buffer or addition of a suitable acid or base is used. The reaction conditions are dependent on the type of association (*) to be formed between the vitamin D compound or analog (D) and the target molecule moiety (T) in order to produce the conjugate.

The molar ratio of T:D in the conjugates of formula (I) is preferably 1:1.

Also within the scope of the present invention are those conjugates in which D is associated with T via connector (herein designated as "G") between D and T; these preferred conjugates are represented by the formula (IV):

(IV)

wherein each G' represents the same or different connecting group; each G" represents the same or different connecting group; g and k each individually represent an integer of 1 or greater; f and h each individually represent an integer of 0 or greater; - indicates a bond in instances where a connecting group is present; n and m are as previously defined herein; and * indicates that the target molecule component is associated with the vitamin D component via connector G' or G" or via both connectors, in instances when both are present. It is understood that D maintains its biological effectiveness in the conjugate or, when D is a previtamin D, isomers to its corresponding vitamin D form having biological effectiveness.

In those cases wherein f or h is zero (and g and k are 1), the conjugate of formula (IV) is simply represented by formula (V):

(V)

In such cases, G is suitably a bifunctional connector, e.g., polyglutamic acid or polyaspartic acid, or a linkage group formed by modification of D and/or T and with subsequent bond formation.

Suitable connecting groups for use in forming the conjugates of formula (IV) are those which link the vitamin D moiety to the target molecule moiety without significantly impairing the biological effectiveness of the vitamin D, and without significantly impairing the affinity of the target molecule component of the conjugate. The connectors form a link between the target molecule moiety and the vitamin D moiety of the conjugate, a link which must be of sufficient stability to remain intact, at least until the conjugate is delivered to the region proximate the target. Under some circumstances, the vitamin D delivered to the target region as part of the conjugate is more effective after at least one connector linking the target molecule moiety and the vitamin D moiety is cleaved. In such cases, at least one such connector is preferably cleaved once the conjugate is delivered proximate the target. In other words, by cleaving the connectors in such cases, one can avoid steric hindrance between the vitamin D and the target molecule moiety which exists in some of the conjugates of the present invention, wherein such steric hindrance reduces the effectiveness of the vitamin D of the conjugate.

In an illustrated embodiment, the conjugate of the present invention includes an agent effective in treating bone disorders, i.e., the conjugate includes a vitamin D moiety and a bone-seeking agent. Preferred among the agents having bone affinity are bisphosphonates ("BP") (also referred to as diphosphonates). For example, a specific bisphosphonate moiety which is suitably operable in the present invention is represented by formula (VI):

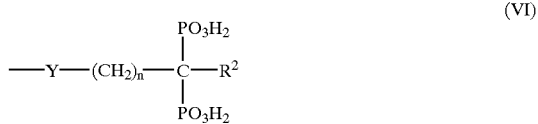

(VI)

wherein $R^2$ is H or OH, Y is NH, O or $NR^8$ wherein $R^8$ is H or $C_1$–$C_4$ alkyl, and n is an integer from 1 to 4. A particularly preferred bone-therapeutic conjugate, wherein T is a BP, is represented by formula (VII):

D-BP (VII)

wherein BP is suitably linked at, e.g., the C-1, C-3, C-17, C-24, or C-25 position of the D moiety.

Specific bone-therapeutic conjugates suitable for use in the present invention, wherein T is a bisphosphonate, include conjugates of formula (VIII):

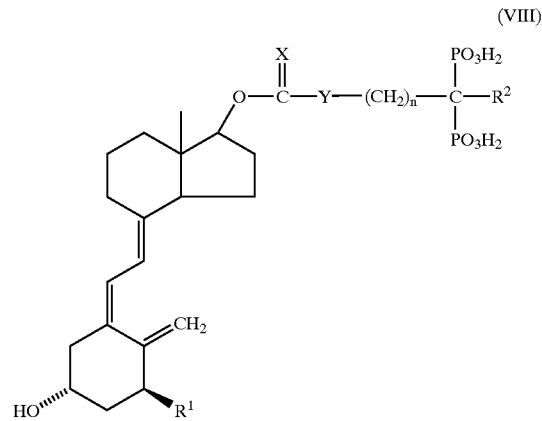

(VIII)

wherein $R^1$ is H or OH; $R^2$ is H or OH; X is O or S; Y is NH, O or NR wherein R is H or $C_1$–$C_4$ alkyl; n is 1–4; and pharmaceutically acceptable salts thereof, i.e., the bisphosphonate is linked to the vitamin D moiety at C-17.

Also provided are conjugates of formula (IX):

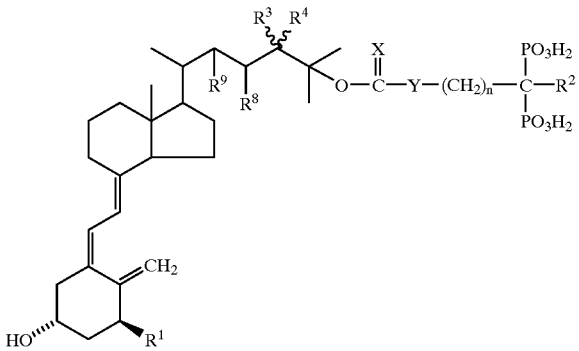

(IX)

wherein $R^1$ is H or OH; $R^2$ is H or OH; $R^3$ is $CH_3$ or H; $R^4$ is H or OH, X is O or S; Y is NH, O or NR wherein R is H or $C_1$–$C_4$ alkyl; n is an integer from 1 to 4; $R^8$ and $R^9$ are each H or taken together form a double bond between C-22 and C-23; and pharmaceutically acceptable salts thereof, i.e., the bisphosphonate is linked at the C-25 position of the vitamin D moiety.

Also provided are conjugates of formula (X):

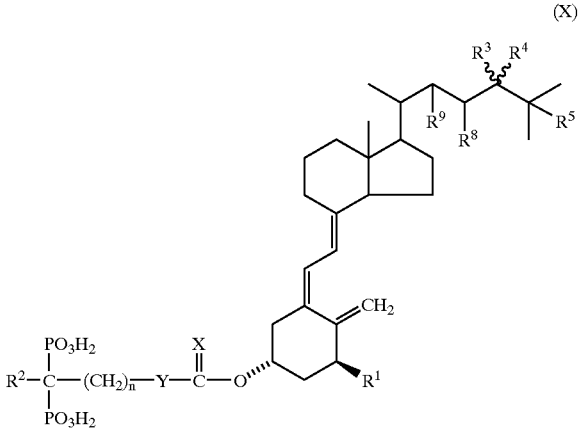

(X)

wherein $R^1$ is H or OH; $R^2$ is H or OH; $R^3$ is $CH_3$ or H; $R^4$ is H or OH, X is O or S; Y is NH, O or NR wherein R is H or $C_1$–$C_4$ alkyl; $R^5$ is H or OH; n is an integer from 1 to 4; $R^8$ and $R^9$ are each H or taken together form a double bond between C-22 and C-23; and pharmaceutically acceptable salts thereof, i.e., the bisphosphonate is linked to the vitamin D moiety at C-3.

Also provided are conjugates of formula (XI):

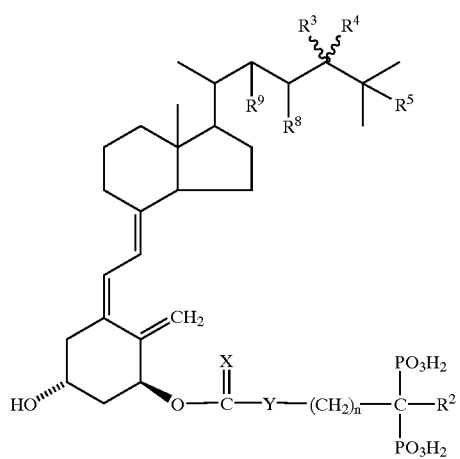

(XI)

wherein $R^2$ is H or OH; $R^3$ is $CH_3$ or H; $R^4$ is H or OH, X is O or S; Y is NH, O or NR wherein R is H or $C_1$–$C_4$ alkyl; $R^5$ is H or OH, n is an integer from 1 to 4, $R^8$ and $R^9$ are each H or taken together form a double bond between C-22 and C-23; and pharmaceutically acceptable salts thereof, i.e., the bisphosphonate linkage is at C-1 of the vitamin D moiety.

It is noted that typically the linkage between the bisphosphonate moiety and the vitamin D moiety is through a hydroxyl on the vitamin D where the hydroxyl is converted to a

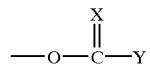

group and is linked to the amine or hydroxy group, i.e., Y, of the bisphosphonate to form a carbamate-type or carbonate-type linkage. X can be O or S. For example, a hydroxyl group may be contained in the vitamin D structure at C-1, C-3, C-24, C-25, and conjugation can be effected at any hydroxyl position but is suitably one of the above.

Synthesis of the conjugates of formula (I), wherein T is a bisphosphonate, is accomplished according to the schema presented in FIGS. 1–6. In general terms, the synthesis includes conversion of a hydroxyl in the vitamin D to a haloformate (e.g., a chloroformate) or thioformate group with subsequent reaction with the appropriate amino or hydroxyl group of the bisphosphonate to form a carbamate, thiocarbamate, carbonate or thiocarbonate linkage. If $R^2$ is hydroxy or the vitamin D compound contains one or more hydroxyl groups in addition to the desired hydroxyl group, these can be protected by conventional hydroxy-protecting groups, such as benzyl, silyloxy, etc., prior to the reaction that converts the desired hydroxyl to a haloformate or thioformate group.

Specifically, in the illustrated embodiment, the starting vitamin D compound or analog (when appropriate, hydroxyl protected) is reacted with phosgene to form a chloroformate, the chloroformate is reacted with an aminobutyl-1,1-bisphosphonate to form a carbamate linkage. Any protected hydroxyls are then deprotected.

FIG. 1 is an illustrative scheme for the synthesis of a conjugate of $1\alpha,24$-$(OH)_2D_2$-aminoalkyl and 1,1-bisphosphonate. As seen in FIG. 1, the $1\alpha,24$-$(OH)_2D_2$ starting material is protected by silyloxyl groups in the C-1 and C-3 positions. The protected D compound (1) is reacted with phosgene in toluene to form the chloroformate (2). The chloroformate (2) is reacted with tetraisopropyl 4-aminobutyl-1,1-bisphosphonate (i.e., hydroxyl-protected) in dichloromethane, and the reaction mix is purified via flash chromatography to yield the protected conjugate (4). The protected conjugate (4) is reacted with tetrahydroform (THF) and tetrabutylammonium fluoride (TBAF) to deprotect the C-1 and C-3 hydroxyls to yield the tetraisopropyl ester of the conjugate (5). The tetraisopropyl ester (5) is hydrolyzed with trimethyl silylbromide to form the conjugate bisphosphonic acid structure (6). Compound (6) and 9-acetylantracene in methanol are irradiated, filtered, concentrated and lyophilized to yield the conjugate (7).

The syntheses illustrated in FIGS. 2–6 are discussed in detail in the Examples section, below.

Also, preferred among the conjugates of formula (I) are those in which T is DHEA. The common steriodal structure of DHEA has a 17-keto group and a 1-hydroxy group. Either of these groups may suitably be linked to hydroxylated positions on the vitamin D, e.g., through ether or ester-type linkages. Reactions for such linkages are well known.

Also desirable among the conjugates of formula (I) are those wherein T is a metal ion, M. Metal ions are known to target many tissue sites, e.g., strontium ion to bone. The conjugates may take the form of direct complexes between a vitamin D moiety and the metal ion wherein the moiety has a negatively charged terminal group, e.g., one having one or more carboxyl groups at C-24, C-25, etc., generally D-X$^-$. The conjugate may be represented by the formula (XII):

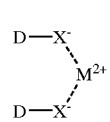

(XII)

wherein X is a negatively charged group such as a carboxyl, —$CO_2^-$, and M is a divalent metal ion.

Alternatively, the conjugate may be of the form of formula (V) wherein D and M are associated by a connector, e.g., an amino acid. For example, it has been disclosed that metal ion-amino acid chelates are capable of targeting tissue site delivery. See, e.g., U.S. Pat. Nos. 4,863,898; 4,176,564; and 4,172,072, each of which is incorporated herein by reference. For example, magnesium-lysine chelates have been shown to target bone; and zinc and methionine have been shown to target skin. Such chelates are of the form

wherein M is the metal ion and AA is an amino acid residue, (e.g. lysine, arginine, etc.), and * indicates an association of the amino acid residue (AA) with the metal ion (M). In the conjugates of the present invention, the amino acid of the metal-amino acid chelate is linked to the vitamin D moiety through the amide-type linkage shown above in the case of when T is bisphosphonate. The conjugates are represented by the formula (XIII):

(XIII)

wherein D is a vitamin D moiety having a group capable of forming a linkage to an amino acid, e.g., a hydroxy group;

(AA) is the amino acid residue, and M is a metal ion, preferably a divalent ion such as $Sr^{2+}$, $Zn^{2+}$, $Mg^{2+}$, $Fe^2$, $Cu^{2+}$, $Mn^{2+}$, $Ca^{2+}$, $Cu^{2+}$, $Co^{2+}$, $Cr^{2+}$ or $Mo^{2+}$. More specifically, conjugates are provided in the form represented by the formula (XIV):

(XIV)

wherein D, M, AA, and * are as defined above.

Also preferred among the conjugates of formula (I) are those wherein T is an antibody. Antibodies or antibody fragment which may be used in such preferred conjugates can be prepared by techniques well known in the art. An example of suitable antibodies are immunoglobins, such as IgG, IgA, IgD and IgE. High specificity monoclonal antibodies can be produced by hybridization techniques well known in the art. See, e.g., Kohler et al., 245 Nature (1975) 495–497; and 6 Eur. J. Immunol. (1 976)(511–519, both of which are incorporated herein by reference. Such antibodies normally may have a highly specific reactivity. Polyclonal antibodies are also suitable for use as the target molecule component of the conjugate. However, when the target molecule moiety is an antibody, it is most preferably a monoclonal antibody (Mab).

Selected monoclonal antibodies are highly specific for a single epitope, making monoclonal antibodies particularly useful as the targeting molecule components of the conjugates of this invention. Conjugates of vitamin D and monoclonal antibodies can be targeted to specific sites within a target region, such as specific vitamin D receptors on the surface of cancerous tissue or in bone tissue. Methods for isolating and producing monoclonal or polyclonal antibodies to specific antigens, such as antibodies to selected target tissue or even to specific target proteins are known. See, e.g., Molecular Cloning, 2n ed., Sambrook et al., eds., Cold Spring Harbor Lab. Press 1989, § 18.3 et seq. Polyclonal antibodies can also be utilized and can be produced more cheaply than monoclonal antibodies. But, polyclonal antibodies inherently are less specific targeting molecules. Nonetheless, it is possible to produce large amounts of monoclonal antibodies suitable for use in the conjugates of the present invention by tissue culture (e.g., a hybridoma cell line).

Conjugates of the present invention produced using such antibody targeting molecules can be directed against, e.g., cells, organs, tumors, differentiation and other cell membrane antigens, polynucleic acids such as DNA and RNA or any biologically active molecule. Antibodies to vitamin D receptors of target cells of interest may be suitable for use in the conjugates of this invention.

For those conjugates in accordance with the present invention, when T is a monoclonal antibody, the T*D association is suitably done via a connector "G", e.g., a biotin-avidin linkage represented by G'-G", using biotin-avidin methodologies known in the art. Such a conjugate based on a connector, e.g., vitamin D-biotin-avidin-antibody, is suitably represented as

[D-G']*[G"-T]

Figure 7:
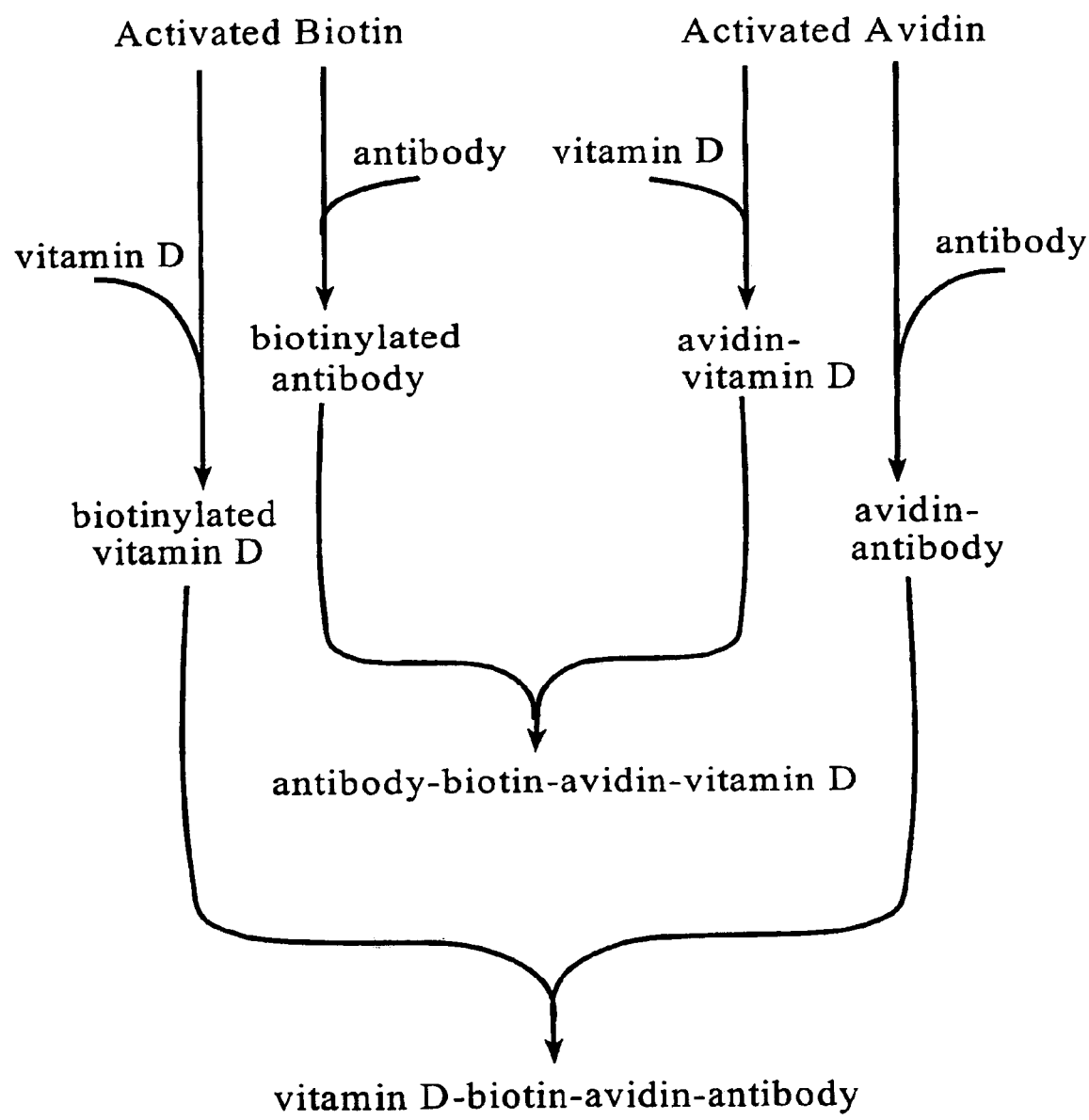
FIG. 7 is a schematic diagram-for preparation of a conjugate of vitamin D and a monoclonal antibody, utilizing a biotin-avidin connector.

A schematic diagram for the coupling of antibodies to vitamin D compounds or analogs using, e.g., biotin-avidin conjugates, is given in FIG. 7.

Referring to FIG. 7, avidin possesses a high affinity for the coenzyme biotin. This is a strong, noncovalent interaction which has been exploited for the conjugation of antibodies to various compounds. The biotin or avidin is suitably coupled to either the vitamin D compound or the antibody component. As such, a number of different schemes are possible for linking vitamin D compounds and antibodies. For example, biotin is suitably linked to the antibody to form a biotinylated antibody complex, while the avidin is suitably linked to the vitamin D compound to form an avidin vitamin D complex. The two complexes are subsequently reacted to form an antibody-biotin-avidin-vitamin D conjugate. A vitamin D-biotin-avidin-antibody conjugate is formed in a similar manner as shown in FIG. 7.

It may be desirable to conjugate hormones or other agents (designated as "A") to the conjugates of formula (I), to form a bifunctional conjugate represented by formula (XV)

$$(D)_m *(T)_n *(A)_p \qquad (XV)$$

wherein A represents a therapeutic agent other than vitamin D and p is an integer of 1 or greater, D, T, m and n are as previously defined herein, with the proviso that D and A maintain their biological effectiveness, and * indicates that the target molecule moiety is associated with the vitamin D moiety and with the therapeutic agent other than vitamin D. For example, a bifunctional conjugate of formula (XV) is one that has the ability to deliver vitamin D to bone as well as another osteogenic agent such as an estrogen.

Thus, included within the scope of the present invention are conjugates of formula (XV) which are bone-therapeutic conjugates wherein A is a hormone or other agents which are known to ameliorate bone diseases or disorders. Such bone agents may include conjugated estrogens or their equivalents, antiestrogens, calcitonin, bisphosphonates, calcium supplements, cobalamin, pertussis toxin, boron, DHEA and other bone growth factors such as transforming growth factor beta, activin or bone morphogenic protein.

Also provided in the present invention are conjugates of formula (XV) which are antiproliferative conjugates wherein A is a cytotoxic agent. Such agents include estromustene, phosphate, prednimustine, cisplatin, S-fluorouracil, melphalan, hydroxyurea, mitomycin, idarubicin, methotrexate, adriamycin and daunomycin.

Included within the scope of the present invention are all possible enantiomers of any conjugate of the invention which exhibits optical isomerism and all possible geometeric isomers due to a cis-trans configuration at double bonds. Additionally, all pharmaceutically acceptable salts of compounds described herein, such as sodium, potassium, lithium, ammonium salts of the compounds, and the like.

The magnitude of a prophylactic or therapeutic dose of the conjugates in accordance with the present invention will vary with the nature or the severity of the condition to be treated and with the particular composition and its route of administration. In general, the daily dose range for use in bone diseases lies within the range of about 0.025 nmol/kg of body weight to about 2.5 nmol/kg. The daily dose for treatment of hyperproliferative diseases, such as cancers, is in the range of about 0.025 nmol/kg to about 5 nmol/kg of body weight.

The conjugates of formula (I) are useful as active compounds in pharmaceutical compositions having reduced side effects and low toxicity as compared with the known analogs of active forms of vitamin $D_3$.

The pharmacologically active conjugates of this invention can be processed in accordance with conventional methods of pharmacy to produce medicinal agents for administration to patients, e.g., mammals including humans. Any suitable route of administration may be employed for providing an effective dosage of the conjugate. For example, oral, rectal, topical, parenteral, intravenous, intramuscular, subcutaneous, ocular, nasal, buccal, and the like may be employed.

Pharmaceutical compositions of the present invention include the conjugate of the present invention as an active ingredient or a pharmaceutically acceptable salt thereof, and may also contain a pharmaceutically acceptable carrier and optionally other therapeutic ingredients. The compositions are those suitable for the various routes of administration described herein, although the most suitable route in any given case will depend on the nature and severity of the condition being treated and on the nature of the active ingredient. They are conveniently presented in unit dosage form.

Suitable pharmaceutically acceptable carriers for use in the composition or method of the present invention include, but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring and flavoring. Additionally, the conjugate of the present invention may be coated or shielded to prevent immunogenicity or reticuloandothelial (RES) response by, e.g., the liver. Agents which can be used for this purpose include polyethylene glycol (PEG) and others known in the art.

In another aspect, the present invention is a method of site-specific delivery of a vitamin D moiety to a tissue of interest in a patient, comprising: (1) providing a conjugate of a vitamin D moiety and at least one target molecule moiety in a pharmaceutically acceptable carrier; and (2) administering a therapeutically effective dose of the conjugate of the present invention described herein. However, the conjugate is preferably delivered in one of the following forms, depending upon the specific method of administration.

For parenteral application, particularly suitable are injectable, sterile solutions, preferably oily or aqueous solution, as well as suspensions, emulsions, or implants, including suppositories. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired. Because of their ease of administration, tablets and capsules represent the most advantageous oral dosage unit.

For rectal administration, conjugates are formed into a pharmaceutical composition containing a suppository base such as cacao oil or other triglycerides. To prolong storage life, the composition advantageously includes an antioxidant, such as ascorbic acid, butylated hydroxyanisole or hydroquinone.

Suitable topical formulations include transdermal devices, aerosols, creams, ointments, lotions, dusting powders and the like.

Oral administration of the pharmaceutical compositions of the present invention is preferred. The daily dosage of the compounds according to this invention generally is about 0.025 to about 2.5 nmol/kg, preferably about 0.025 to about 1 nmol/kg. Generally, the conjugates of this invention are dispensed by unit dosage form in a pharmaceutically acceptable carrier. For treatment of hyperproliferative diseases such as cancers, the enteral dosage of the conjugates of formula (I), is about 1 mmol to about 100 nmol per unit dosage; for bone diseases, about 0.5 nmol to 50 nmol per unit dosage.

In addition, those skilled in the art will also appreciate that such dosages may be encapsulated in time release, e.g., sustained, delayed or directed release delivery systems such as a liposome delivery system, polysaccharides exhibiting a slow release mechanism, salistic or other polymer implants or microspheres, as well as those where the active ingredient is suitably protected with one or more differentially degradable coatings, e.g., by microencapsulation, enteric coating, multiple coatings, etc., and such means effect continual dosing of compositions contained therein. For example, an enteric coating is suitably one which is resistant to disintegration in gastric juice. It is also possible to freeze-dry the active ingredient and use the lyophilizate obtained, e.g., for the preparation of products for injection.

It will further be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, sex, body weight, general state of health, on diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

The present invention is further explained by the following examples which should not be construed by way of limiting the scope of the present invention.

EXAMPLE 1

Synthesis of 1α-(OH)-24-aminoalkyl-1,1-bisphosphonate-$D_2$ conjugate (7)

Reference is made to the reaction scheme of FIG. 1. A solution of the known alcohol (1) (1.0 g, 1.52 mmol) in toluene (5 mL) is added to 22 mL of a 12.5% solution of phosgene in toluene and the solution is stirred at room temperature for 20 hrs. The reaction mixture is concentrated under reduced pressure to provide the chloroformate (2).

Pyridine (0.18 mL, 2.2 mmol) is added to a solution of (2) (1.1 g, 1.53 mmol) and tetraisopropyl 4-aminobutyl-1,1-bisphosphonate 3 (see, Saari et al., U.S. Pat. No. 5,183,815) (0.92 g, 2.2 mmol) in $CH_2Cl_2$ (12 mL), and the mixture is stirred at room temperature for three days. The reaction mixture is concentrated under reduced pressure, and the residue is purified by flash chromatography over silica gel, utilizing methanol/chloroform as the eluent, to yield compound (4).

A solution of compound (4) (0.80 g, 0.74 mmol) in tetrahydrofuran (THF) (10 mL) and tetrabutylammonium fluoride (TBAF) (2.2 mL of a 1.0 M THF solution, 2.2 mmol) is stirred at room temperature for 24 hrs. The reaction mixture is diluted with water (30 mL) and extracted with $CH_2Cl_2$ (3×40 mL). The combined $CH_2Cl_2$ fractions are dried over anhydrous sodium sulfate, filtered, and the filtrate is concentrated under reduced pressure. The residue is purified by flash chromatography over silica gel, utilizing methanol/chloroform as the eluent, to yield tetraisopropyl ester compound (5).

Trimethylsilylbromide (0.39 mL, 2.92 mmol) is added to a solution of the tetraisopropyl ester compound (5) (0.5 g, 0.58 mmol) in $CH_2Cl_2$ (6 mL), and the mixture is stirred at room temperature for 24 hrs. under an inert atmosphere. The reaction mixture is concentrated under reduced pressure and the residue is diluted with water (15 mL). The mixture is filtered and the filtrate lyophilized to provide compound (6).

A solution of compound (6) (250 mg, 0.36 mmol) and 9-acetylanthracene (21 mg) in methanol (93 mL) is placed in an ACE 500-mL photo reactor and the solution is purged with nitrogen for 15 min. The reaction mixture is cooled to 0° C. and irradiated with a 400 W Hanovia lamp filtered through uranyl glass for 2 hrs. The reaction mixture is filtered, and the filtrate is concentrated under reduced pressure. The residue is diluted with water (10 mL). The mixture is filtered and the filtrate lyophilized to provide the above-titled conjugate (7).

EXAMPLE 2

Synthesis of 1-aminoalkyl-1,1-bisphosphonate-24-(OH)-$D_2$ (16)

Figure 2A:
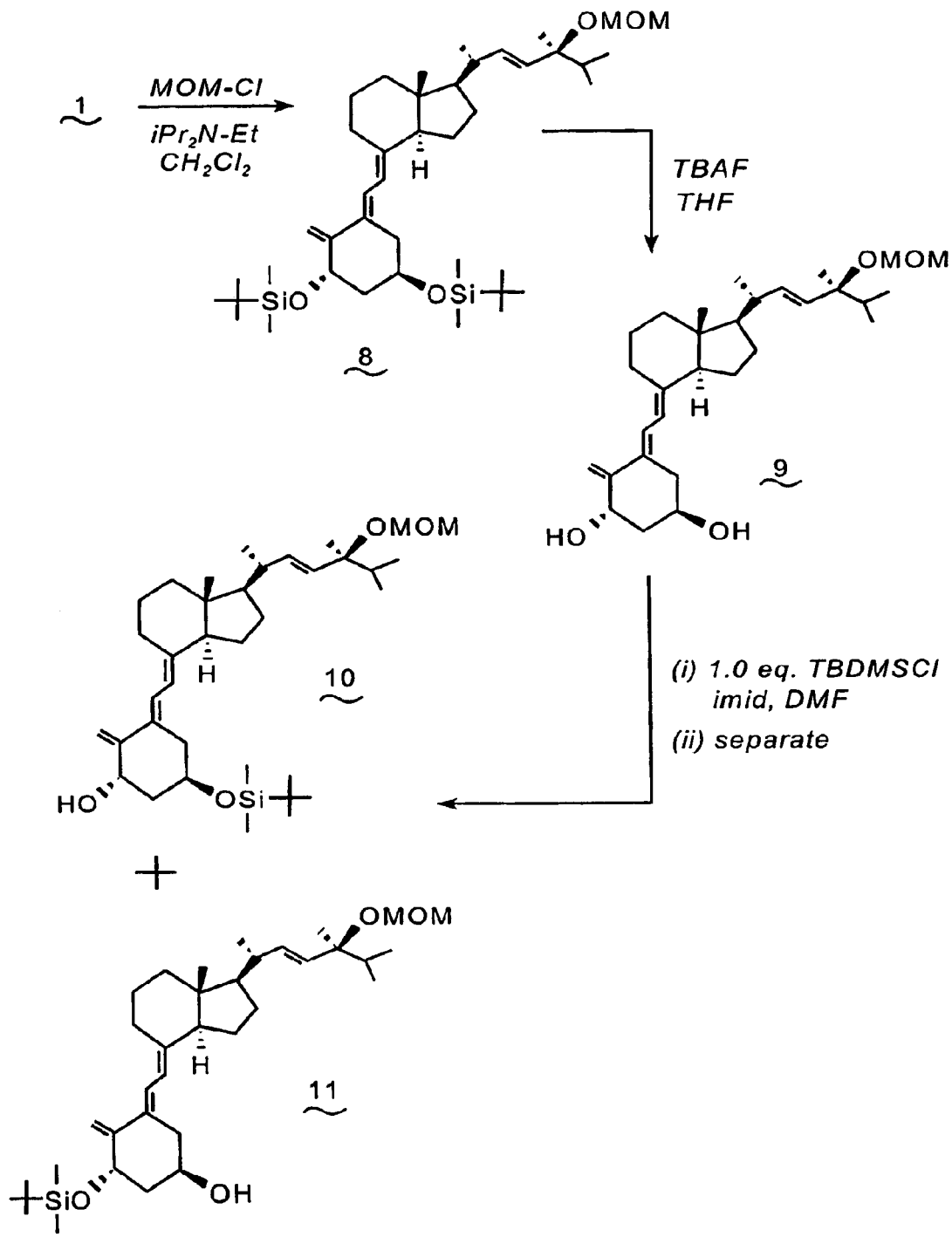
FIGS. 2A and 2B illustrate a reaction scheme for the preparation of a conjugate of 1α,24-$(OH)_2D_2$ and aminoalkyl-1,1-bisphosphonate linked at C-1 of the vitamin D moiety.
Figure 2B:
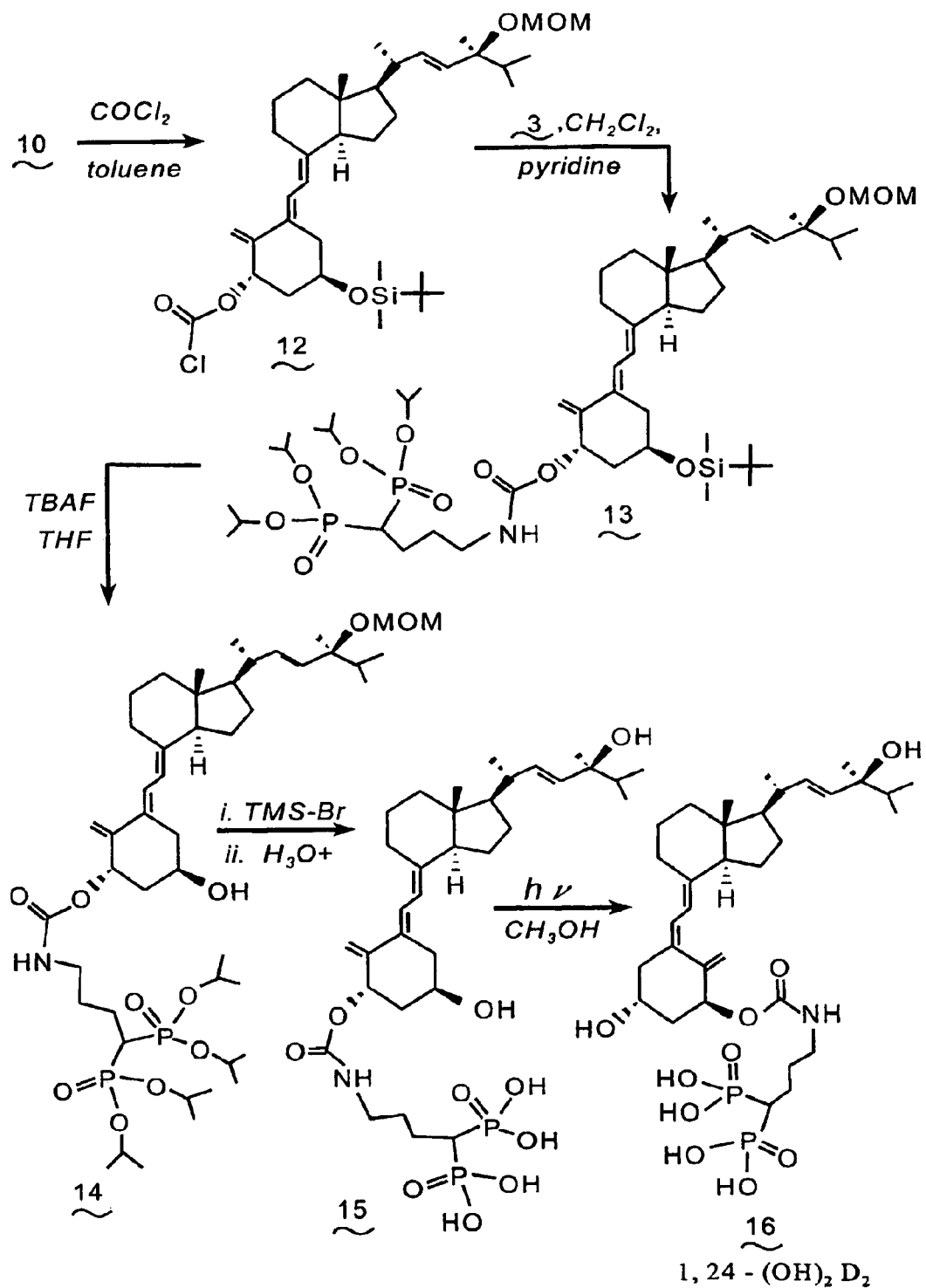

Reference is made to the reaction scheme depicted in FIGS. 2A & 2B. To a 0° C. solution of compound (1) (2.0 g, 3.04 mmol), and N,N-diisopropylethylamine (0.78 g, 6.1 mmol) in $CH_2Cl_2$ (25 mL) is added chloromethyl methyl ether (0.29 g, 3.6 mmol). The resulting reaction mixture is stirred at 0° C. for 1 hr., then at room temperature for 7 hrs, prior to dilution with water (30 mL). The separated aqueous phase is extracted with $CH_2Cl_2$ (3×25 mL), and the combined organic phases are dried over anhydrous sodium sulfate, filtered, and the filtrate is concentrated in vacuo. The residue is purified by flash chromatography over silica gel to provide compound (8).

A solution of compound (8) (1.99 g, 2.84 mmol) in THF (38 mL) and TBAF (8.4 mL of a 1.0 M THF) is stirred at room temperature for 24 hrs. The reaction mixture is diluted with water (100 mL), and extracted with $CH_2Cl_2$ (3×100 mL). The combined $CH_2Cl_2$ phases are dried over anhydrous sodium sulfate, filtered, and the filtrate is concentrated under reduced pressure. The residue is purified by flash chromatography over silica gel, utilizing methanol/chloroform as the eluent, to yield the diol compound (9).

To a solution of diol (9) (1.25 g, 2.64 mmol), N,N-dimethylformamide (20 mL), and imidazole (0.54 g, 7.93 mmol) is added tert-butyldimethylsilyl chloride (0.40 g, 2.64 mmol). The reaction mixture is stirred at room temperature for 6 hrs., prior to dilution with water (60 mL) and extraction with $CH_2Cl_2$ (3×70 mL). The combined organic phases are washed with brine (50 mL), dried over anhydrous sodium sulfate, filtered, and the filtrate is concentrated under reduced pressure. The residue is purified by flash chromatography over silica gel, to provide two products separately. They are identified in FIG. 2A as alcohol (10) and alcohol (11).

As illustrated at the top of FIG. 2B, a solution of alcohol (10) (0.5 g, 0.85 mmol) in toluene (2.5 mL) is added to 12.3 mL of a 12.5% solution of phosgene in toluene and the solution is stirred at room temperature for 20 hrs. The reaction mixture is concentrated under reduced pressure to provide chloroformate (12).

Pyridine (0.09 mL, 1.1 mmol) is added to a solution of cloroformate (12) (0.5 g, 0.77 mmol) and tetraisopropyl 4-aminobutyl-1,1-bisphosphonate (3) (0.46 g, 1.1 mmol) in $CH_2Cl_2$ (6 mL) and the mixture is stirred at room temperature for three days. The reaction mixture is concentrated under reduced pressure, and the residue is purified by flash chromatography over silica gel, utilizing methanol/chloroform as the eluent, to yield compound (13).

A solution of compound (13) (0.50 g, 0.49 mmol) in THF (7 mL) and TBAF (0.74 mL of a 1.0 M THF solution, 0.74 mmol) is stirred at room temperature for 24 hrs. The reaction mixture is diluted with water (20 mL) and extracted with $CH_2Cl_2$ (3×30 mL). The combined $CH_2Cl_2$ fractions are dried over anhydrous sodium sulfate, filtered, and the filtrate is concentrated under reduced pressure. The residue is purified by flash chromatography over silica gel, utilizing methanol/chloroform as the eluent, to provide compound (14).

Trimethylsilylbromide (0.26 mL, 1.96 mmol) is added to a solution of tetraisopropyl ester (14) (0.35 g, 0.39 mmol) in $CH_2Cl_2$ (4 mL) and the mixture is stirred at room temperature for 24 hrs. under an inert atmosphere. The reaction mixture is concentrated under reduced pressure and the residue is diluted with water (15 mL) and methanol (3 mL) and is stirred for 8 hrs. The mixture is filtered and the filtrate lyophilized to provide compound (15).

A solution of compound (15) (0.21 g, 0.31 mmol) and 9-acetylanthracene (18 mg) in methanol (80 mL) is placed in an ACE 500-mL photo reactor, and the solution is purged with nitrogen for 15 min. The reaction mixture is cooled to 0° C. and is irradiated with a 400 W Hanovia lamp filtered through uranyl glass for 2 hrs. The reaction mixture is filtered, and the filtrate concentrated under reduced pressure. The residue is diluted with water (10 mL). The mixture is filtered and the filtrate lyophilized to provide the above-titled conjugate (16).

EXAMPLE 3

Synthesis of 1α,24-$(OH)_2$-3-aminoalkyl-1,1-bisphosphonate-$D_2$ (21)

Figure 3:
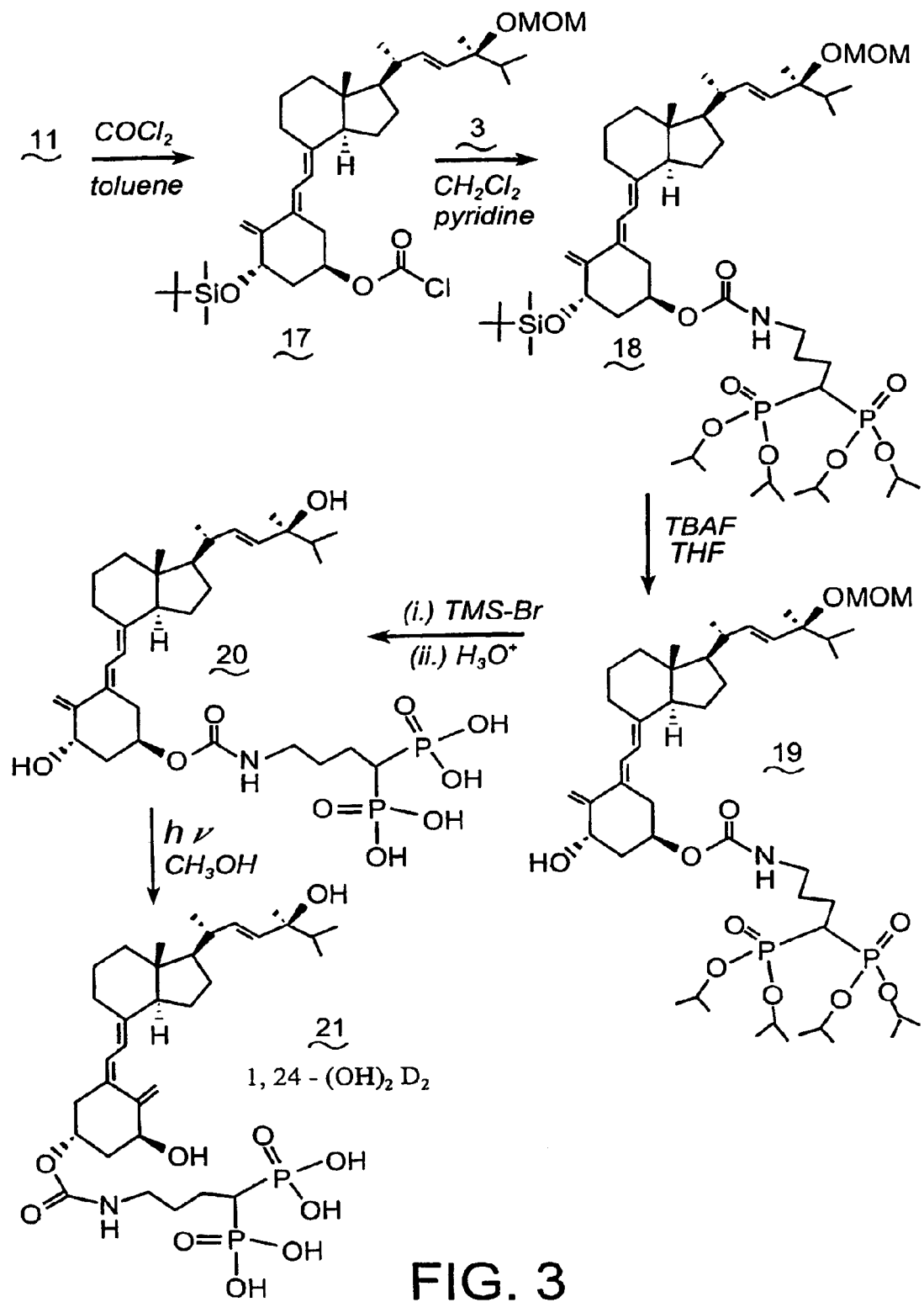
FIG. 3 illustrates a reaction scheme for the preparation of a conjugate of 1α,24-$(OH)_2D_2$ and aminoalkyl-1,1-bisphosphonate linked at C-3 of the vitamin D moiety.

Reference is made to FIG. 3. A solution of alcohol (11) (0.5 g, 0.85 mmol) in toluene (2.5 mL) is added to 12.3 mL of a 12.5% solution of phosgene in toluene and the solution is stirred at room temperature for 20 hrs. The reaction mixture is concentrated under reduced pressure to provide chloroformate (17).

Pyridine (0.081 mL, 1 mmol) is added to a solution of (17) (0.45 g, 0.69 mmol) and tetraisopropyl 4-aminobutyl-1,1-bisphosphonate (0.41 g, 1 mmol) in $CH_2Cl_2$ (5 mL), and the mixture is stirred at room temperature for three days. The reaction mixture is concentrated under reduced pressure, and the residue is purified by flash chromatography over silica gel, utilizing methanol/chloroform as the eluent, to provide compound (18).

A solution of compound (18) (0.47 g, 0.46 mmol) in THF (6.5 mL) and TBAF (0.7 mL of a 1.0 M THF solution, 0.7 mmol) is stirred at room temperature for 24 hrs. The reaction mixture is diluted with water (20 mL) and extracted with $CH_2Cl_2$ (3×30 mL). The combined $CH_2Cl_2$ fractions are dried over anhydrous sodium sulfate, filtered, and the filtrate is concentrated under reduced pressure. The residue is purified by flash chromatography over silica gel, utilizing methanol/chloroform as the eluent, to yield compound (19).

Trimethylsilylbromide (0.23 mL, 1.74 mmol) is added to a solution of tetraisopropyl ester (19) (0.31 g, 0.34 mmol) in $CH_2Cl_2$ (4 mL) and the mixture is stirred at room temperature for 24 hrs under an inert atmosphere. The reaction mixture is concentrated under reduced pressure, and the residue is diluted with water (15 mL) and methanol (3 mL), and stirred for 8 hrs. The mixture is filtered, and the filtrate is lyophiiized to provide compound (20).

A solution of compound (20) (0.21 g, 0.31 mmol) and 9-acetylanthracene (18 mg) in methanol (80 mL) is placed in an ACE 500-mL photo reactor, and the solution is purged with nitrogen for 15 min. The reaction mixture is cooled to 0° C. and irradiated with a 400-W Hanovia lamp filtered through uranyl glass for 2 hrs. The reaction mixture is filtered, and the filtrate is concentrated under reduced pressure. The residue is diluted with water (10 mL). The mixture is filtered, and the filtrate is lyophilized to provide the above-titled conjugate (21).

EXAMPLE 4

Synthesis of 1α-aminoalkyl-1,1-bisphosphonate-25-(OH)-$D_3$ (32)

Figure 4A:
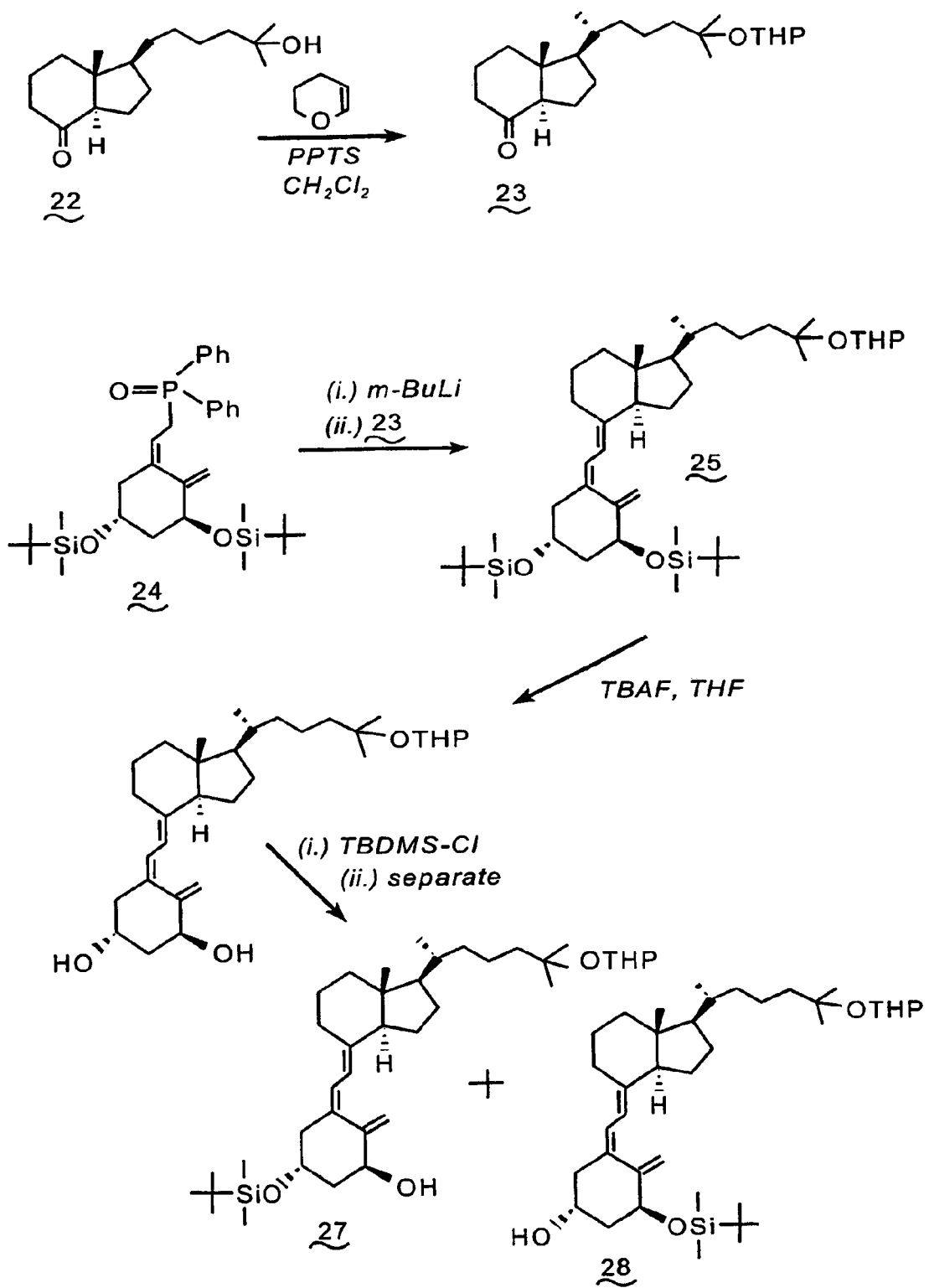
FIGS. 4A and 4B illustrate a reaction scheme for the preparation of a conjugate of 1α,25-dihydroxyvitamin $D_3$ (1α,25-$(OH)_2D_3$) and aminoalkyl-1,1-bisphosphonate linked at C-1 of the vitamin D moiety.
Figure 4B:
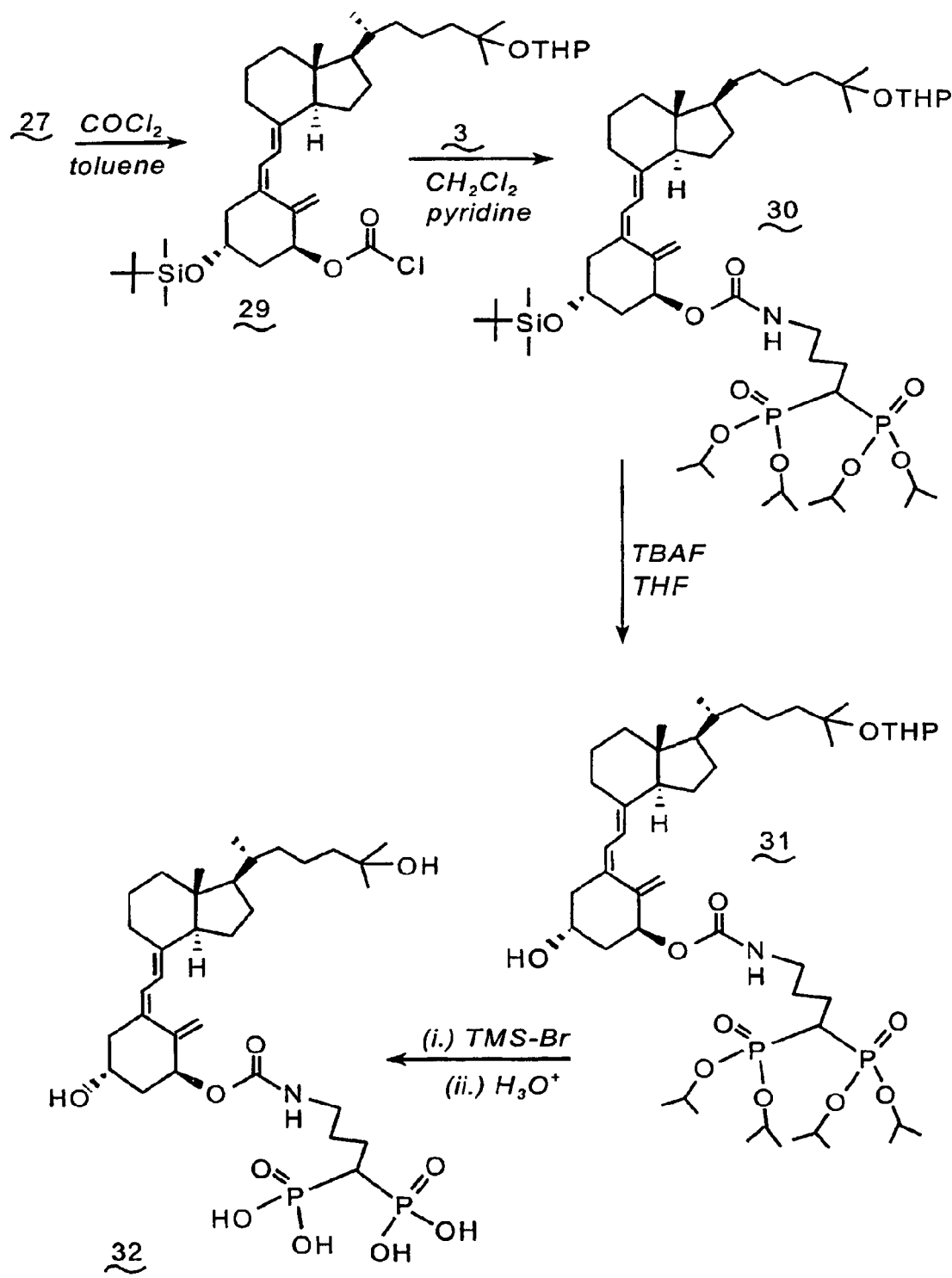

Reference is made to the reaction scheme depicted in FIGS. 4A and 4B. A solution of the known ketone (22) (3.1 g, 11.1 mmol) (see, Baggiolini et al., 51 *J. Org. Chem.* (1986), 3098–3108), incorporated herein by reference, 3,4-dihydro-2H-pyran (1.52 mL, 16.7 mmol), and pyridinium p-toluenesulfonate (0.1 g, 0.4 mmol) are dissolved in $CH_2Cl_2$ (50 mL), and are stirred at room temperature for 24 hrs. The reaction mixture is washed with water (30 mL), and the organic phase is dried over anhydrous sodium sulfate, filtered, and concentrated under reduced pressure. The residue is purified by flash chromatography over silica gel to yield ketone compound (23).

A solution of the known phosphine oxide (24) (1.35 g, 2.32 mmol) in 35 mL of anhydrous THF is cooled to −78° C. and treated with m-butyllithium (1.45 mL of a 1.6 M solution in hexane) dropwise. The anion solution is stirred for 5 min. at −78° C. prior to the addition of ketone (23) (0.57 g, 1.56 mmol) dissolved in anhydrous THF (10 mL) during 10–15 min. The reaction mixture is stirred for 2 hrs at −78° C. then diluted with 2 N sodium potassium tartrate (6 mL) and 2 N potassium bicarbonate (6 mL). The solution is warmed to room temperature and extracted with ethyl acetate (4×25 mL). The combined organic fractions are washed with brine (30 mL), dried over anhydrous sodium sulfate, filtered, and concentrated under reduced pressure. The residue is purified by flash chromatography over silica gel, utilizing ethyl acetate/hexane as eluent, to provide compound (25).

A solution of compound (25) (0.95 g, 1.3 mmol) in THF (17 mL) and TBAF (3.9 mL of a 1.0 M THF solution, 3.9 mmol) is stirred at room temperature for 24 hrs. The reaction mixture is diluted with water (50 mL) and extracted with $CH_2Cl_2$ (3×60 mL). The combined $CH_2Cl_2$ fractions are dried over anhydrous sodium sulfate, filtered, and the filtrate concentrated under reduced pressure. The residue is purified by flash chromatography over silica gel, utilizing methanol/chloroform as eluent, to provide diol compound (26).

To a solution of the diol compound (26) (0.55 g, 1.1 mmol), N, N-dimethylformamide (8 mL), and imidazole (0.255 g, 3.3 mmol) is added tert-butyldimethylsilyl chloride (0.166 g, 1.1 mmol). The reaction mixture is stirred at room temperature for 6 hrs., prior to dilution with water (30 mL) and extraction with $CH_2Cl_2$ (3×40 mL). The combined organic phases are washed with brine (30 mL), dried over anhydrous sodium sulfate, filtered, and concentrated under reduced pressure. The residue is purified by flash chromatography over silica gel, to provide two separate products. They are identified, at the bottom of FIG. 4A, as alcohol (27) and alcohol (28).

A solution of alcohol (27) (0.25 g, 0.41 mmol) in toluene (3 mL) is added to 6 mL of a 12.5% solution of phosgene in toluene, and the reaction mixture is stirred at room temperature for 20 hrs. The reaction mixture is concentrated under reduced pressure to provide chloroformate (29), as shown at the top of FIG. 4B.

Pyridine (0.047 mL, 0.57 mmol) is added to a solution of (29) (0.27 g, 0.4 mmol) and tetraisopropyl 4-aminobutyl-1,1-bisphosphonate (0.24 g, 0.57 mmol) in $CH_2Cl_2$ (4 mL) and the mixture is stirred at room temperature for three days. The reaction mixture is concentrated under reduced pressure, and the residue is purified by flash chromatography over silica gel, utilizing methanol/chloroform as eluent, to provide compound (30).

A solution of compound (30) (0.36 g, 0.35 mmol) in THF (5 mL) and TBAF (0.52 mL of a 1.0 M THF solution, 0.52 mmol) is stirred at room temperature for 24 hrs. The reaction mixture is diluted with water (15 mL) and extracted with $CH_2Cl_2$ (3×25 mL). The combined $CH_2Cl_2$ fractions are dried over anhydrous sodium sulfate, filtered, and concentrated under reduced pressure. The residue is purified by flash chromatography over silica gel, utilizing methanol/chloroform as eluent, to provide compound (31).

Trimethylsilylbromide (0.20 mL, 1.54 mmol) is added to a solution of tetraisopropyl ester (31) (0.28 g, 0.30 mmol) in $CH_2Cl_2$ (4 mL), and the mixture is stirred at room temperature for 24 hrs. under an inert atmosphere. The reaction mixture is concentrated under reduced pressure and the residue diluted with water (15 mL) and methanol (3 mL) and stirred for 0.5 hr. The mixture is filtered, and the filtrate is lyophilized to provide the above-titled conjugate (32).

EXAMPLE 5

Synthesis of 1α,25-$(OH)_2$-3-aminoalkyl-1,1 bisphosphonate-$D_3$ (36)

Figure 5:
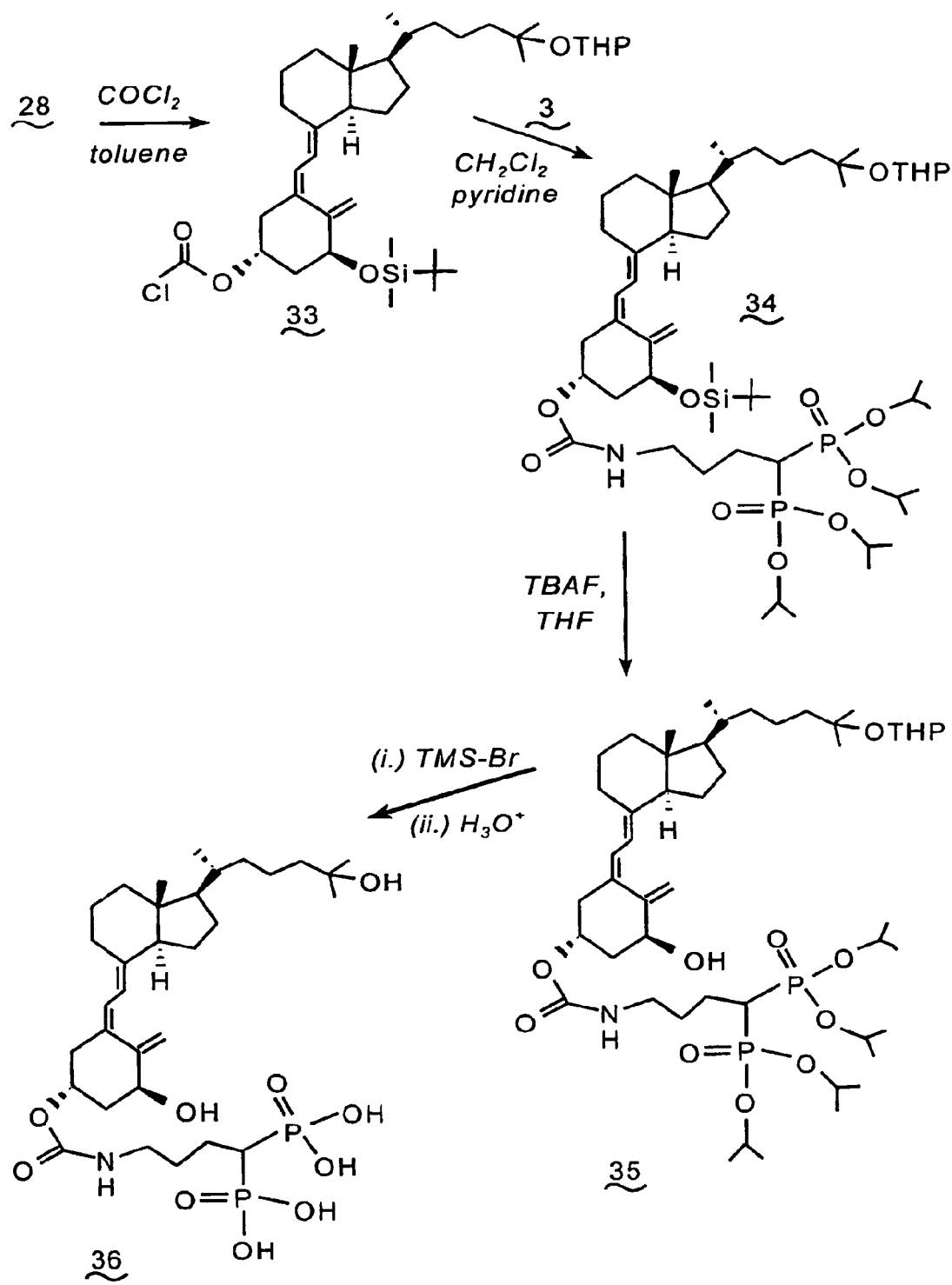
FIG. 5 illustrates a reaction scheme for the preparation of a conjugate of 1α,25-$(OH)_2D_3$ and aminoalkyl-1,1-bisphosphonate linked at the at C-3 of the vitamin D moiety.

Reference is made to FIG. 5. A solution of alcohol (28) (0.26 g, 0.43 mmol) in toluene (3 mL) is added to 6.2 mL of a 12.5% solution of phosgene in toluene and the reaction is stirred at room temperature for 20 hrs. The reaction mixture is concentrated under reduced pressure to provide chloroformate (33).

Pyridine (0.049 mL, 0.59 mmol) is added to a solution of chloroformate (33) (0.28 g, 0.42 mmol) and tetraisopropyl 4-aminobutyl-1,1-bisphosphonate (0.25 g, 0.59 mmol) in $CH_2Cl_2$ (5 mL), and the mixture is stirred at room temperature for three days. The reaction mixture is concentrated under reduced pressure, and the residue is purified by flash chromatography over silica gel, utilizing methanol/chloroform as eluent, to yield compound (34).

A solution of compound (34) (0.37 g, 0.36 mmol) in THF (5 mL) and TBAF (0.54 mL of a 1.0 M THF solution, 0.54 mmol) is stirred at room temperature for 24 hrs. The reaction mixture is diluted with water (15 mL) and extracted with $CH_2Cl_2$ (3×25 mL). The combined $CH_2Cl_2$ fractions are dried over anhydrous sodium sulfate, filtered, and the filtrate concentrated under reduced pressure. The residue is purified by flash chromatography over silica gel, utilizing methanol/chloroform as eluent, to yield tetraisopropyl ester (35).

Trimethylisilylbromide (0.21 mL, 1.60 mmol) is added to a solution of the tetraisopropyl ester (35) (0.29 g, 0.31 mmol) in $CH_2Cl_2$ (5 mL), and the mixture is stirred at room temperature for 24 hrs under an inert atmosphere. The reaction mixture is concentrated under reduced pressure, and the residue is diluted with water (15 mL) and methanol (3 mL) and stirred for 0.5 hr. The mixture is filtered, and the filtrate is lyophilized to provide the above-titled conjugate (36).

EXAMPLE 6

Synthesis of 1α-(OH)-25-aminoalkyl-1,1-bisphosphonate-$D_3$ (41)

Figure 6:
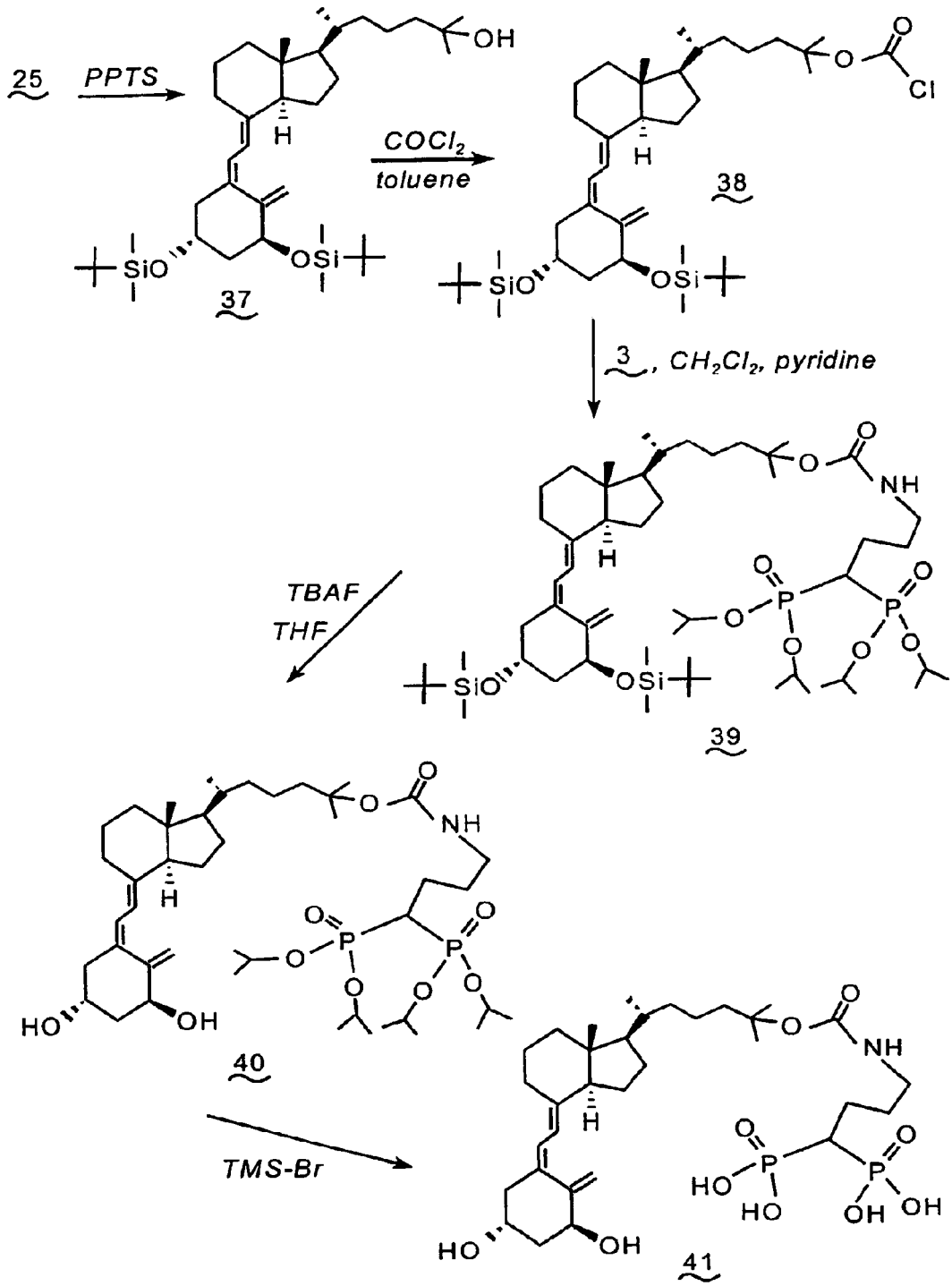
FIG. 6 illustrates a reaction scheme for the preparation of a conjugate of 1α,25-$(OH)_2D_3$ and aminoalkyl-1,1-bisphosphonate linked at C-25 of the vitamin D moiety.

Reference is made to FIG. 6. To a solution of ether (25) (1.31 g, 1.8 mmol) in methanol (10 mL) and water (2 mL) is added pyridinium p-toluenesulfonate hydrate (0.034 g, 0.18 mmol). The reaction mixture is stirred at room temperature for 1 hr, diluted with water (20 mL) and extracted with $CH_2Cl_2$ (3×30 mL). The combined organic phases are dried over anhydrous sodium sulfate, filtered, and concentrated in vacuo. The residue is purified by flash chromatography over silica gel, utilizing methanol/chloroform as eluent, to provide alcohol (37).

A solution of alcohol (37) (1.09 g, 1.7 mmol) in toluene (9 mL) is added to 25 mL of a 12.5% solution of phosgene in toluene, and the reaction is stirred at room temperature for 20 hrs. The reaction mixture is concentrated under reduced pressure to provide chloroformate (38).

Pyridine (0.19 mL, 2.32 mmol) is added to a solution of cloroformate (38) (1.17 g, 1.65 mmol) and tetraisopropyl 4-aminobutyl-1,1-bisphosphonate (0.98 g, 2.32 mmol) in $CH_2Cl_2$ (20 mL), and the mixture is stirred at room temperature for three days. The reaction mixture is concentrated under reduced pressure, and the residue is purified by flash chromatography over silica gel, utilizing methanol/chloroform as eluent, to yield alcohol (39).

A solution of alcohol (39) (1.61 g, 1.5 mmol) in THF (20 mL) and TBAF (4.5 mL of a 1.0 M THF solution, 4.5 mmol) is stirred at room temperature for 24 hrs. The reaction mixture is diluted with water (60 mL) and extracted with $CH_2Cl_2$ (3×60 mL). The combined $CH_2Cl_2$ phases are dried over anhydrous sodium sulfate, filtered, and the filtrate is concentrated under reduced pressure. The residue is purified by flash chromatography over silica gel, utilizing methanol/chloroform as eluent, to provide tetraisopropyl ester compound (40).

Trimethylsilylbromide (0.75 mL, 5.68 mmol) is added to a solution of the tetraisopropyl ester compound (40) (0.93 g, 1.1 mmol) in $CH_2Cl_2$ (20 mL), and the mixture is stirred at room temperature for 24 hrs under an inert atmosphere. The reaction mixture is concentrated under reduced pressure and the residue is diluted with water (30 mL). The mixture is filtered and the filtrate is lyophilized to provide the above-titled compound (41).

In summary, the present invention provides vitamin D conjugates useful in targeting applications. The conjugates include a vitamin D moiety and a targeting molecule moiety having affinity for a tissue of interest. The conjugates are characterized by an ability for site-specific targeting of vitamin D compounds, e.g., a conjugate of vitamin D and a bone affinity agent is designed to transport and deliver vitamin D to bone tissue.

While the present invention has now been described and exemplified with some specificity, those skilled in the art will appreciate the various modifications, including variations, additions, and omissions, that may be made in what has been described.

We claim:

1. A conjugate comprising 1α-(OH)-24-aminoalkyl-1,1-bisphosphonate-$D_2$, 1-aniinoalkyl-1,1-bisphosphonate-24-(OH)-$D_2$, 1α,24-(OH)$_2$-3-aminoalkyl-1,1-bisphosphonate-$D_2$, 1α-aminoalkyl-1,1-bisphosphonate-25-(OH)-$D_3$, 1α,25-(OH)$_2$-3-aminoalkyl-1,1-bisphosphonate-$D_3$, 1α-(OH)-25-aminoalkyl-1,1-bisphosphonate-$D_3$, or a combination thereof.

2. A pharmaceutical composition comprising:

a conjugate comprising 1α-(OH)-24-aminoalkyl-1,1-bisphosphonate-$D_2$, 1-aminoalkyl-1,1-bisphosphonate-24-(OH)-$D_2$, 1α,24-(OH)$_2$-3-aminoalkyl-1,1-bisphosphonate-$D_2$, 1α-aminoalkyl-1,1-bisphosphonate-25-(OH)-$D_3$, 1α,25-(OH)$_2$-3-aminoalkyl-1,1-bisphosphonate-$D_3$, 1α-(OH)-25-aminoalkyl-1,1-bisphosphonate-$D_3$, or a combination thereof, and a suitable pharmaceutically acceptable carrier.

3. The pharmaceutical composition of claim 2, further comprising an additional therapeutic agent.

4. The pharmaceutical composition of claim 3, wherein the therapeutic agent comprises at least one of conjugated estrogens or their equivalents, antiestrogens, calcitonin, bisphosphonates, calcium supplements, cobalamin, pertussis toxin, boron, dehydroepiandrosterone, transforming bone growth factor beta, activin, bone morphogenic protein and a combination thereof.

5. The pharmaceutical composition of claim 2, further comprising a differentially degradable coating encapsulating the conjugate for time release delivery of the conjugate.

6. The pharmaceutical composition of claim 5, wherein said coating is an enteric coating.

* * * * *